United States Patent
Ehara et al.

(10) Patent No.: US 7,956,181 B2
(45) Date of Patent: Jun. 7, 2011

(54) TREHALOSE FATTY ACID ESTER COMPOSITION

(75) Inventors: Taro Ehara, Odawara (JP); Kyu Yamaguchi, Tokyo (JP)

(73) Assignee: The Nisshin Oillio Group, Ltd.

( * ) Notice: Subject to any disclaimer, the term of this patent is extended or adjusted under 35 U.S.C. 154(b) by 432 days.

(21) Appl. No.: 12/128,023

(22) Filed: May 28, 2008

(65) Prior Publication Data

US 2008/0234392 A1    Sep. 25, 2008

Related U.S. Application Data

(63) Continuation of application No. PCT/JP2006/323824, filed on Nov. 29, 2006.

(30) Foreign Application Priority Data

Nov. 30, 2005  (JP) .................. 2005-346021

(51) Int. Cl.
*C07H 13/02* (2006.01)
*C07H 13/06* (2006.01)
*C07H 13/10* (2006.01)

(52) U.S. Cl. ..................................... 536/119

(58) Field of Classification Search .............. None
See application file for complete search history.

(56) References Cited

U.S. PATENT DOCUMENTS

| | | | | |
|---|---|---|---|---|
| 4,307,229 A | * | 12/1981 | Liav et al. | 536/119 |
| 4,684,719 A | * | 8/1987 | Nishikawa et al. | 536/119 |
| 4,973,489 A | * | 11/1990 | Meyer et al. | 426/611 |
| 5,006,514 A | * | 4/1991 | Kato et al. | 514/53 |
| 5,049,664 A | | 9/1991 | Yoshinaga et al. | |
| 5,906,924 A | | 5/1999 | Mandai et al. | |
| 6,504,003 B1 | | 1/2003 | Trout et al. | |
| 6,890,543 B2 | | 5/2005 | Minami et al. | |
| 2005/0106198 A1 | | 5/2005 | Gotou et al. | |

FOREIGN PATENT DOCUMENTS

| | | |
|---|---|---|
| EP | 1 488 850 A1 | 12/2004 |
| JP | 59-157097 | 9/1984 |
| JP | 60-258195 | 12/1985 |
| JP | 03-047193 | 2/1991 |
| JP | 11-171727 | 6/1999 |
| JP | 11-209231 | 8/1999 |
| JP | 2001158718 | 6/2001 |
| WO | 99/48946 A2 | 9/1999 |
| WO | 03/082454 A1 | 10/2003 |
| WO | 2006/003992 A1 | 1/2006 |
| WO | 2007/063902 A1 | 6/2007 |

OTHER PUBLICATIONS

Hatzios et al., "PapA3 Is an Acyltransferase Required for Polyacyltrehalose Biosynthesis in *Mycobacterium tuberculosis*" Journal of Biological Chemistry (2009) vol. 284 No. 19, pp. 12745-12751.*
Chinese Patent Office, Office Action issued on Chinese Patent Application No. 200680044620.9, dated Feb. 12, 2010.
Japanese Patent Office, International Search Report in Application No. PCT/JP2006/323824 dated Feb. 27, 2007.
Haruo Okumura et al., "Determination of Sucrose Fatty Acid Esters by High-Performance Liquid Chromatography," Journal of Oleo Science, vol. 50, No. 4 (2001) pp. 249-254.

* cited by examiner

*Primary Examiner* — Eric S Olson
(74) *Attorney, Agent, or Firm* — Wood, Herron & Evans, LLP

(57) ABSTRACT

Provided is a pigment dispersant having excellent pigment dispersibility thus allowing a larger amount of pigments to be blended in various cosmetics, and capability of imparting good sense of use, make-up lasting, odor, and stability over time to the cosmetic. A trehalose fatty acid ester composition prepared by esterifying trehalose with a fatty acid having 8 to 22 carbon atoms, which has a hydroxyl value of 20 to 500, and the total amount of a diester, a triester, a tetraester and a pentaester in the trehalose fatty acid esters of 10 to 100% by area; and a cosmetic including the trehalose fatty acid ester composition.

5 Claims, 1 Drawing Sheet

TREHALOSE FATTY ACID ESTER COMPOSITION

TECHNICAL FIELD

The present invention relates to a trehalose fatty acid ester composition having excellent pigment dispersibility, which is suitable as a dispersant for a cosmetic, etc., and to a cosmetic containing the same.

The present application claims benefit of priority of PCT/JP2006/323824, as filed on Nov. 29, 2006, and Japanese Patent Application No. 2005-346021, as filed on Nov. 30, 2005, the disclosures of which are herein incorporated by reference in their entirety.

BACKGROUND ART

Conventionally, powders, which are typically exemplified by pigments, have been used in a variety of applications including cosmetics, paints, inks, pencils, memory materials, lubricants, medicines, and foods, and various studies have been performed to obtain stable dispersion. In order to disperse uniformly the powders such as pigments in oily components, it is required to improve the wettability of the powders, thereby inhibiting aggregation of the powders and stabilizing the dispersion. Extensive studies have been conducted to achieve these objects.

For example, in the field of cosmetics, powders such as pigments are blended thereinto so as to provide a desired color to the cosmetics, and to improve sense of use. For this reason, in order to provide cosmetics of stable quality, it is necessary to uniformly and stably disperse powders such as pigments in oily components. As a way of improving the dispersibility of the pigment itself, for example, there has been performed a treatment of a surface of a pigment with a silane coupling agent, etc. However, if the degree of surface treatment is increased, although the dispersing ability is improved, there are problems in that the cosmetics blended with such a pigment give poorer fitting to skin, and when used for a prolonged period of time, floating, unevenness, or the like, of cosmetics is caused.

On the other hand, an attempt has been made to uniformly disperse a pigment in oily components by using as a pigment dispersant a polar oil in which a hydroxyl group remains and further using a pigment in combination with the pigment dispersant. For example, as a pigment dispersant, there is known diglyceryl triisostearate (see Patent Document 1), or sucrose fatty acid esters such as sucrose stearic acid ester and sucrose oleic acid ester.

[Patent Document 1] Japanese Laid-Open Patent Application No. 2001-158718

However, the invention as described in Patent Document 1 limits the amount of a pigment to be blended to 30% by mass or less, and from the review of Examples, the amount of the pigment dispersant required to satisfy the pigment dispersibility is assumed to be around 20% by mass. Recently, various qualities are required for cosmetics, and the role of the pigment selected to be blended is increasingly becoming important. In addition, the amount of pigment to be blended tends to increase. If the amount of pigment to be blended into the cosmetics is increased, there occurs aggregation of the pigment, etc., thereby causing a problem such as deterioration of dispersibility. In the case of using a conventional pigment dispersant, as the amount of the pigment to be blended is increased, the amount of the pigment dispersant to be blended should be increased, correspondingly. However, since it is also required to blend other components (for example, an oil gelling agent, a feeling improving agent, a moisturizer, and cosmetic components) in the cosmetics, there are problems such that there is a limit in the amount of each of the pigment dispersant and the pigment to be blended, respectively, and that it is difficult to satisfy both of the pigment dispersibility and the sense of use, etc. at the same time.

In addition, although sucrose stearic acid ester has excellent dispersion ability, it is mostly in the state of a solid form having high crystallinity. Thus, if the amount of esters blended in the cosmetics is increased, it is difficult to retain its own shape, for example, crystals precipitate over time. Furthermore, when a liquid sucrose oleic acid ester is blended into the cosmetics, rancidity is generated over time, thus causing an odor problem.

As such, a dispersant for pigments, etc., which provides various cosmetics excellent in the sense of use, make-up lasting, odor, stability over time, and the like, by being blended therewith, and realizes blending of powders in a large amount and has excellent dispersibility, is not yet found. In practice, conventional cosmetics have been developed under limitations in the blended amount of a pigment, etc.

If a dispersant for a pigment, etc. that can satisfy all of the above-described characteristics is developed, such a dispersant can be used in various applications including cosmetics, paints, inks, pencils, memory materials, lubricant, medicines, and foods, which require powders such as pigments to be blended therein, and further, it can be expected to develop a product having an excellent color tone or sense of use, that has an equivalent or higher content of powders than that of those conventionally used. Furthermore, if such dispersant is used for cosmetics, a cosmetic excellent in sense of use, make-up lasting, odor, stability over time, etc. can be provided. Therefore, in the field of cosmetics, it is expected that the problems which have not been overcome until now will be solved.

DISCLOSURE OF THE INVENTION

Accordingly, it is an object of the present invention to provide a composition that has excellent dispersibility of a pigment, etc. so that powders may be blended into a cosmetic in a larger amount, and for example, if blended into cosmetics, can provide a cosmetic excellent in sense of use, make-up lasting, odor, and stability over time.

The inventors of the present invention have conducted extensive studies, and as a result, they have found that the problem can be solved by a trehalose fatty acid ester composition, prepared by esterifying trehalose with a fatty acid having 8 to 22 carbon atoms, which has a hydroxyl value in a specific range, and has the total amount of a diester, a triester, a tetraester and a pentaester in the trehalose fatty acid esters in a specific range. Based on this, the present invention has been completed.

Specifically, in order to solve the above-described problem, a first aspect of the present invention provides a trehalose fatty acid ester composition, prepared by esterifying trehalose with a fatty acid having 8 to 22 carbon atoms, which has a hydroxyl value of 20 to 500, and the total amount of a diester, a triester, a tetraester and a pentaester in the trehalose fatty acid esters of 10 to 100% by area, as measured by carrying out high-performance liquid chromatography analysis under the following two measurement conditions, and expressed in area percentage (% by area) determined using the following determination method.

<Measurement Condition for High-Performance Liquid Chromatography Analysis>

Measurement condition A: Measurement condition for high-performance liquid chromatography analysis to determine the % by area of a monoester, a diester, a triester, and a polyester in the trehalose fatty acid ester composition.

Column: Four styrene divinylbenzene-based GPC columns, connected in a series, each being 7.8 mm in inner diameter; 300 mm in length, and 5 μm in size
  Mobile phase: Tetrahydrofuran
  Column temperature: 40° C.
  Flow rate of mobile phase: 0.5 mL/min
  Detection: differential refraction index (RI)
Measurement condition B: Measurement condition for high-performance liquid chromatography analysis to determine the ratio of a tetraester, a pentaester, a hexaester, a heptaester, and an octaester in a polyester in the trehalose fatty acid ester composition.
  Columns: ODS column, which is 4.6 mm in inner diameter; 150 mm in length, and 5 μm in size.
  Mobile phase: Tetrahydrofuran:methanol=55:45 (volume ratio)
  Column temperature: 40° C.
  Flow rate of mobile phase: 0.8 mL/min
  Detection: differential refraction index (RI)
<Method for Determining Area Percentage (% by Area) of Each Ester>
(1) Method for Determining the % by Area of a Monoester, a Diester, and a Triester:
  A percentage of the peak area of each of raw materials, a monoester, a diester, and a triester, relative to a total peak area, obtained as measured by means of high-performance liquid chromatography analysis using the GPC columns under measurement condition A, is taken as a % by area of each ester.
(2) Method for Determining the % by Area of a Polyester:
  A percentage (X) of a total peak area of components other than raw materials, a monoester, a diester, and a triester, relative to a total peak area, obtained as measured by means of high-performance liquid chromatography analysis using the GPC columns under measurement condition A, is taken as a % by area of a polyester.
(3) Method for Determining the Ratio of a Tetraester, a Pentaester, a Hexaester, a Heptaester, and an Octaester in a Polyester:
  A total peak area of a tetraester, a pentaester, a hexaester, a heptaester, and an octaester, obtained as measured by means of high-performance liquid chromatography analysis using the ODS columns under measurement condition B, is taken as (Y), and a ratio of the peak area of each of tetraester, a pentaester, a hexaester, a heptaester, and an octaester relative to (Y) is taken as a ratio of each of a tetraester, a pentaester, a hexaester, a heptaester, and an octaester in a polyester.
(4) Method for Determining the % by Area of Each of a Tetraester, a Pentaester, a Hexaester, a Heptaester, and an Octaester:
  A value obtained by multiplying the % by area (X) of a polyester as determined in (2) with the ratio of the peak area of each of a tetraester, a pentaester, a hexaester, a heptaester, and an octaester in polyester as determined in (3), is taken as a % by area of each of a tetraester, a pentaester, a hexaester, a heptaester, and an octaester.
(5) Method for Determining the Total Amount of a Diester, a Triester, a Tetraester, and a Pentaester:
  A % by area obtained from a sum of the % by area of a diester and a triester as determined in (1) and the % by area of a tetraester and a pentaester as determined in (4) is taken as the total amount of a diester, a triester, a tetraester, and a pentaester in the trehalose fatty acid esters.

A second aspect of the present invention provides a trehalose fatty acid ester composition obtained from trehalose and a fatty acid having 8 to 22 carbon atoms, which has the total amount of a diester, a triester, and a tetraester of 2 to 40% by area, as measured by carrying out high-performance liquid chromatography analysis under the following two measurement conditions, and expressed in area percentage (% by area) determined using the following determination method, and has the total amount of a hexaester, a heptaester, and an octaester of 30 to 98% by area, as measured by carrying out high-performance liquid chromatography analysis under the following two measurement conditions, and expressed in area percentage (% by area) determined using the following determination method.

<Measurement Condition for High-Performance Liquid Chromatography Analysis>
  Measurement Condition A:
  A measurement condition for high-performance liquid chromatography analysis to determine the % by area of a monoester, a diester, a triester, and a polyester in the trehalose fatty acid ester composition.
    Column: Four styrene divinylbenzene-based GPC columns, connected in a series, each being 7.8 mm in inner diameter; 300 mm in length, and 5 μm in size
    Mobile phase: Tetrahydrofuran
    Column temperature: 40° C.
    Flow rate of mobile phase: 0.5 mL/min
    Detection: differential refraction index (RI)
  Measurement Condition B:
  A measurement condition for high-performance liquid chromatography analysis to determine the % by area of a tetraester, a pentaester, a hexaester, a heptaester, and an octaester of a polyester in the trehalose fatty acid ester composition.
    Columns: ODS column which is 4.6 mm in inner diameter; 150 mm in length, and 5 μm in size
    Mobile phase: Tetrahydrofuran: methanol=55:45 (volume ratio)
    Column temperature: 40° C.
    Flow rate of mobile phase: 0.8 mL/min
    Detection: differential refraction index (RI)
<Method for Determining Area Percentage (% by Area) of Each Ester>
(1) Method for Determining the % by Area of a Monoester, a Diester, and a Triester:
  A percentage of the peak area of each of raw materials, a monoester, a diester, and a triester, relative to a total peak area, obtained as measured by means of high-performance liquid chromatography analysis using the GPC columns under measurement condition A, is taken as a % by area of each ester.
(2) Method for Determining the % by Area of a Polyester:
  A percentage (X) of a total peak area of components other than raw materials, a monoester, a diester, and a triester, relative to a total peak area, obtained as measured by means of high-performance liquid chromatography analysis using the GPC columns under measurement condition A, is taken as a % by area of a polyester.
(3) Method for Determining the Ratio of a Tetraester, a Pentaester, a Hexaester, a Heptaester, and an Octaester in a Polyester:
  A total peak area of a tetraester, a pentaester, a hexaester, a heptaester, and an octaester, obtained as measured by means of high-performance liquid chromatography analysis using the ODS columns under measurement condition B, is taken as (Y), and a ratio of the peak area of each of tetraester, a pentaester, a hexaester, a heptaester, and an octaester relative to (Y) is taken as a ratio of each of a tetraester, a pentaester, a hexaester, a heptaester, and an octaester in a polyester.

(4) Method for Determining the % by Area of Each of a Tetraester, a Pentaester, a Hexaester, a Heptaester, and an Octaester:

A value obtained by multiplying the % by area (X) of a polyester as determined in (2) with the ratio of the peak area of each of a tetraester, a pentaester, a hexaester, a heptaester, and an octaester in polyester as determined in (3), is taken as a % by area of each of a tetraester, a pentaester, a hexaester, a heptaester, and an octaester.

(5-1) Method for Determining the Total Amount of a Diester, a Triester, and a Tetraester:

A % by area obtained from a sum of the % by area of a diester and a triester as determined in (1) and the % by area of a tetraester as determined in (4) is taken as the total amount of a diester, a triester, and a tetraester in the trehalose fatty acid esters.

(5-2) Method for Determining the Total % by Area of a Hexaester, a Heptaester, and an Octaester:

A % by area obtained from a sum of a hexaester, a heptaester, and an octaester as determined in (4) is taken as the total amount of a hexaester, a heptaester, and an octaester in the trehalose fatty acid esters.

A third aspect of the present invention provides the trehalose fatty acid ester composition as described in the first or second aspects of the present invention, wherein the fatty acid having 8 to 22 carbon atoms is isostearic acid.

A fourth aspect of the present invention provides the trehalose fatty acid ester composition as described in any one of the first through third aspects of the present invention, which is used as a dispersant.

A fifth aspect of the present invention provides a cosmetic containing a trehalose fatty acid ester composition as described in any one of the first through fourth aspects of the present invention.

Since the trehalose fatty acid ester composition of the present invention (hereinafter, simply referred to as the composition) has excellent dispersibility, it is suitable particularly for a dispersant for a pigment, etc., and the use of the composition enables, for example, to blend larger amounts of the pigment in the cosmetics. Moreover, it can provide a cosmetic excellent in the sense of use, make-up lasting, odor, and stability over time, and accordingly, it is possible to prepare a cosmetic having a desired color tone with high quality. Furthermore, in the preparation of the cosmetics, there is no need to use particular operations or facilities, and conventionally known ones can be employed. As a result, it is possible to provide a cosmetic that is excellent in terms of cost.

BEST MODE FOR CARRYING OUT THE INVENTION

Figure 1:
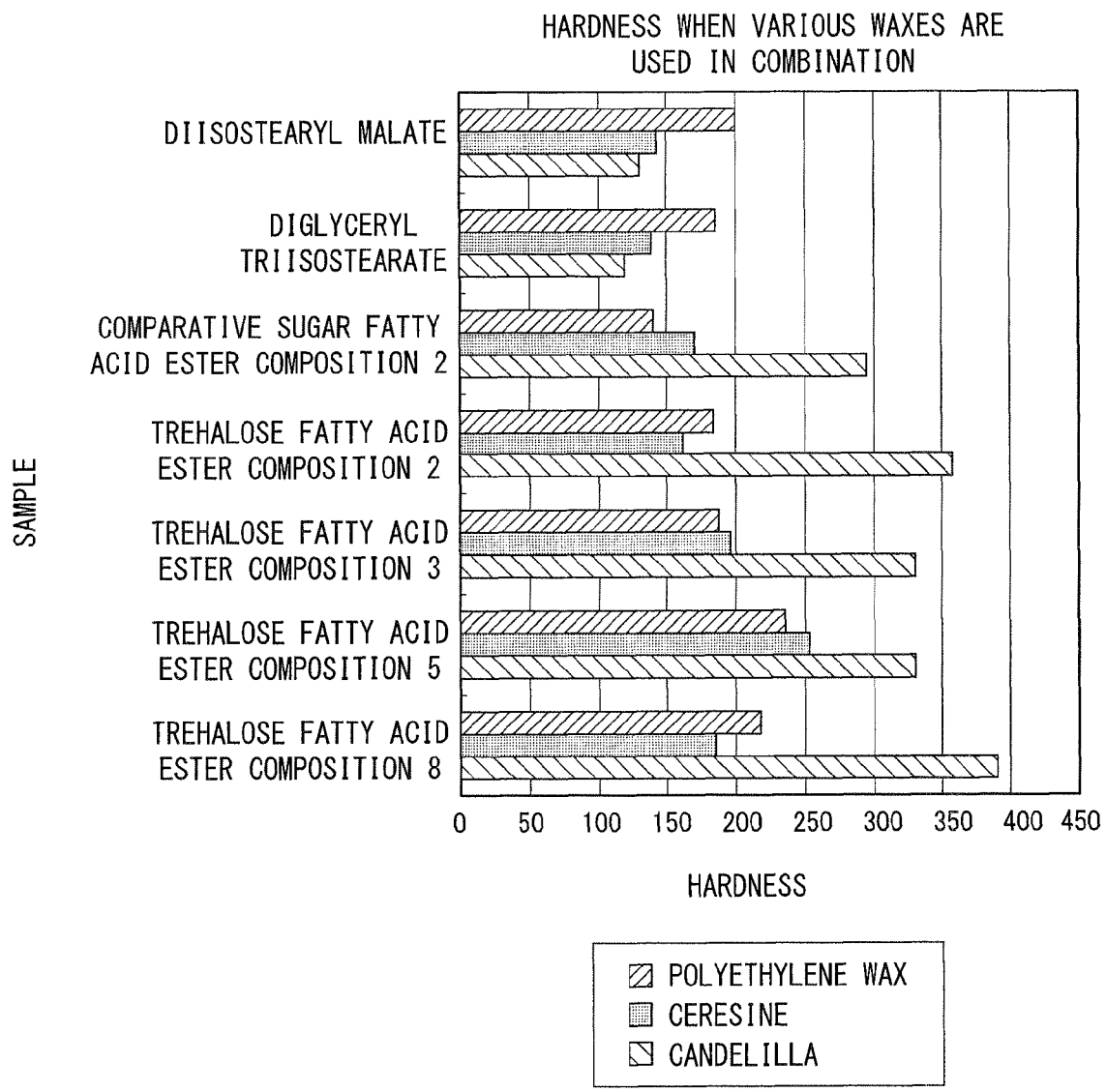
FIG. 1 is a graph showing the evaluation results of the hardness in the case of using the trehalose fatty acid ester composition of the present invention and various waxes in combination.

Hereinbelow, the present invention is described in detail.

The hydroxyl value as denoted below refers to a value determined by the Hydroxyl Value Determination in General Tests in the Standards of Cosmetic Ingredients.

Unless otherwise specifically defined, the amount of each of the trehalose fatty acid ester refers to an area percentage (% by area) determined by high-performance liquid chromatography analysis (hereinafter simply referred to as HPLC). HPLC can be carried out by using a differential refraction index (RI) method with reference to "Determination of Sucrose Fatty Acid Ester by High-performance Liquid Chromatography; J. Oleo Sci., Vol. 50, No. 4(2001)". For analysis of each ester in the trehalose fatty acid ester composition, all of the esters cannot be separated under only one measurement condition, and thus, a combination of two measurement conditions using GPC columns and ODS columns can be used to analyze all of the esters. The % by area of the remaining raw materials, a monoester, a diester, and a triester can be determined under the measurement condition using GPC columns. Since a tetraester, a pentaester, a hexaester, a heptaester, and an octaester cannot be separated from each other under the measurement condition using GPC columns, the value can be taken for a polyester (a mixture of a tetraester, a pentaester, a hexaester, a heptaester, and an octaester). Since a tetraester, a pentaester, a hexaester, a heptaester, and an octaester can be separated from each other under the measurement condition using an ODS column, the % by area of a tetraester, a pentaester, a hexaester, a heptaester, and an octaester can be determined from the ratio of a tetraester, a pentaester, a hexaester, a heptaester, and an octaester in the polyester as determined under the measurement condition using an ODS column, and from the % by area of the polyester as determined under the measurement condition using GPC columns. Herein, the analysis methods (measurement conditions) and the determination methods are described below in detail.

Furthermore, as used in the present invention, the ester of fatty acid having 8 to 22 carbon atoms refers to an ester containing a fatty acid residue having 8 to 22 carbon atoms.

<Measurement Condition for High-Performance Liquid Chromatography Analysis>

A measurement condition for high-performance liquid chromatography analysis to determine the % by area of a monoester, a diester, a triester, and a polyester in the trehalose fatty acid ester composition (Measurement Condition A) is as follows. Further, the polyester refers to a mixture of a tetraester, a pentaester, a hexaester, a heptaester, and an octaester.

Column: Four styrene divinylbenzene-based GPC columns, connected in a series, each being 7.8 mm in inner diameter; 300 mm in length, and 5 μm in size Mobile phase: Tetrahydrofuran Column temperature: 40° C.

Flow rate of mobile phase: 0.5 mL/min

Detection: differential refraction index (RI)

A measurement condition for high-performance liquid chromatography analysis to determine the % by area of a tetraester, a pentaester, a hexaester, a heptaester, and an octaester of a polyester in the trehalose fatty acid ester composition (Measurement Condition B) is as follows.

Columns: ODS column which is 4.6 mm in inner diameter; 150 mm in length, and 5 μm in size Mobile phase: Tetrahydrofuran:methanol=55:45 (volume ratio)

Column temperature: 40° C.

Flow rate of mobile phase: 0.8 mL/min

Detection: differential refraction index (RI)

<Method for Determining Area Percentage (% by Area) of Each Ester>

A method for determining the % by area of a monoester, a diester, and a triester is as follows (Determination Method (1)).

A percentage of the peak area of each of raw materials, a monoester, a diester, and a triester, relative to a total peak area, obtained as measured by means of high-performance liquid chromatography analysis using the GPC columns under measurement condition A, is taken as a % by area of each ester.

A method for determining the % by area of a polyester is as follows (Determination Method (2)).

A percentage (X) of a total peak area of components other than raw materials, a monoester, a diester, and a triester, relative to a total peak area, obtained as measured by means of high-performance liquid chromatography analysis using the GPC columns under measurement condition A, is taken as a % by area of a polyester.

A method for determining the ratio of a tetraester, a pentaester, a hexaester, a heptaester, and an octaester in a polyester is as follows (Determination Method (3)).

A total peak area of a tetraester, a pentaester, a hexaester, a heptaester, and an octaester, obtained as measured by means of high-performance liquid chromatography analysis using the ODS column under measurement condition B, is taken as (Y), and a ratio of the peak area of each of tetraester, a pentaester, a hexaester, a heptaester, and an octaester relative to (Y) is taken as a ratio of each of a tetraester, a pentaester, a hexaester, a heptaester, and an octaester in a polyester.

A method for determining the % by area of each of a tetraester, a pentaester, a hexaester, a heptaester, and an octaester is as follows (Determination Method (4)).

A value obtained by multiplying the % by area (X) of a polyester as determined in (2) with the ratio of the peak area of each of a tetraester, a pentaester, a hexaester, a heptaester, and an octaester in polyester as determined in (3), is taken as a % by area of each of a tetraester, a pentaester, a hexaester, a heptaester, and an octaester.

A method for determining the total amount of each of the esters is as follows (Determination Method (5)).

A % by area obtained from a sum of the % by area of all the esters as determined in Determination Method (1) or Determination Method (4) is taken as the total amount of each of the esters.

A % by area obtained by adding the % by area of, for example, a diester, a triester, a tetraester, and a pentaester can be determined by adding the % by area of a diester and a triester as determined in Determination Method (1), and the % by area of a tetraester and a pentaester as determined in Determination Method (4).

The fatty acid having 8 to 22 carbon atoms that is used in the present invention is preferably a saturated fatty acid, due to its high antioxidizing stability over time. The linear, saturated fatty acid having 8 to 22 carbon atoms is not particularly limited, and preferable examples thereof include stearic acid, palmitic acid, myristic acid, lauric acid, and behenic acid. Among these, stearic acid is more preferable.

Furthermore, the fatty acid having 8 to 22 carbon atoms that is used in the present invention is more preferably a branched, saturated fatty acid, since the trehalose fatty acid ester composition obtained by esterification of trehalose with this acid has low crystallinity. The branched, saturated fatty acid having 8 to 22 carbon atoms is not particularly limited, but preferable examples thereof include isostearic acid, isopalmitic acid, isononanoic acid, isooctylic acid, and the like Among these, isostearic acid is more preferable. For example, the trehalose fatty acid ester composition of the present invention obtained by esterifying trehalose with isostearic acid has high solubility in oil, and even with a wide range of hydroxyl values, is in a non-crystalline solid through liquid states. When the composition is blended into a cosmetic, problems in stability, such as precipitation of crystals over time, are overcome. For this reason, the trehalose fatty acid ester composition of the present invention is particularly preferable since the amount thereof to be used is not limited, and the composition can exhibit the functions retained by the composition of the present invention, such as dispersibility of a pigment, to a most extent.

Furthermore, the fatty acid having 8 to 22 carbon atoms that is used in the present invention, may be a mixture of a linear, saturated fatty acid, and a branched, saturated fatty acid. The use of the branched saturated fatty acid alone, or in a mixture with a linear, saturated fatty acid, as the fatty acid having 8 to 22 carbon atoms that is used in the present invention is preferable, since it results in lower crystallinity of the trehalose fatty acid ester composition of the present invention, thereby providing a cosmetic that is expected to have improved preservation stability over time. These fatty acids may be used alone, or in combination of two or more kinds thereof. In particular, preferred are isostearic acid alone, or a mixture of isostearic acid and stearic acid.

As such, in the case of using a mixture of the fatty acids having 8 to 22 carbon atoms that are used in the present invention, the ratio of the branched, saturated fatty acid in the linear, saturated fatty acid and the branched, saturated fatty acid in the mixture is preferably 30% by mass or more. By setting such a ratio, for example, even when the trehalose fatty acid ester composition of the present invention is blended into the cosmetic in a large amount, the cosmetic would have stable shape-retaining ability.

The trehalose that is used in the present invention is not limited in its source and quality, and a commercially available product itself can be used for this.

Esterification of trehalose and a fatty acid having 8 to 22 carbon atoms that is carried out in the present invention may be performed by a conventionally known method, for example, by esterifying trehalose with a fatty acid having 8 to 22 carbon atoms, or by transesterifying trehalose with a fatty acid having 8 to 22 carbon atoms. For example, as the fatty acid, a free carboxylic acid may be used, and a carboxylic acid ester for transesterification thereof with trehalose is not particularly limited. Here, as the carboxylic acid ester, an ester of a lower alcohol such as methanol and ethanol is preferred, since the alcohol resulting from the reaction may be easily removed by concentration under reduced pressure.

Further, if necessary, an additive such as a catalyst can be used. The reaction condition is not particularly limited, and may be appropriately adjusted such that the hydroxyl value of the resulting trehalose fatty acid ester composition may be in the range from 20 to 500, depending on the raw materials.

For example, in the esterification of trehalose and a fatty acid methyl as raw materials, the amount of the trehalose and the fatty acid methyl to be used, respectively, is preferably set for the mass ratio of trehalose/fatty acid methyl to be in a range of 13/100 to 80/100, and in the case of using dimethyl sulfoxide as a solubilizer, it is preferable to perform the reaction under reduced pressure at a reaction temperature of 70 to 120° C. with a reaction time of 8 to 12 hours. Furthermore, in the case of using a microemulsion process in which trehalose is dissolved in water and made into an emulsion with a fatty acid methyl using a surfactant such as a saponified fatty acid, followed by the reaction under heating and reduced pressure, it is preferable to perform the reaction under reduced pressure at a reaction temperature of 90 to 170° C. with a reaction time of 24 to 60 hours. Furthermore, as the catalyst used, an alkali catalyst such as potassium carbonate, sodium carbonate, potassium hydroxide, and sodium hydroxide is preferable. If the reaction temperature is lower or the reaction time is shorter than each of the above-described ranges, the reaction does not proceed completely, and further if the reaction temperature is higher or the reaction time is longer than each of the above-described ranges, there are several problems, for example, the compatibility between the trehalose and the fatty acid methyl as the raw materials is reduced, and thus these are separated from each other, the reaction does not proceed completely, and the trehalose and the trehalose fatty acid methyl ester as the raw materials are decomposed. As a result, a desired composition cannot be obtained. For this reason, it is more preferable to perform the reaction under the above-described reaction condition.

After the reaction, as a method for separating out a trehalose fatty acid ester composition as a target, a conventionally known method may be applied. For example, after the reaction solution is washed with warm water, etc. to remove an aqueous phase, then an organic phase is concentrated under reduced pressure to distill off moisture, the reaction solvent, or the like. Further, if necessary, the resultant is diluted with an organic solvent, and subject to decoloration and deodoration treatments, and then distillation treatment, thereby obtaining a target. Furthermore, it is purified, for example, by column purification, using silica gel, etc., and the purified products are mixed to allow them to have a desired composition.

The trehalose fatty acid ester composition of the present invention has a hydroxyl value of 20 to 500, and the total amount of a diester, a triester, a tetraester, and a pentaester in the ester composition of 10 to 100% by area. If the hydroxyl value is less than 20, dispersibility of the pigment is insufficient. Furthermore, if the hydroxyl value is more than 500, dispersibility of the pigment is insufficient, and solubility in oil is poor. Thus, it becomes difficult to use the composition, for example, for an oily cosmetic, including a make-up cosmetic containing an oily component in a large amount. Further, if the total amount of a diester, a trimester, a tetraester, and a pentaester is less than 10% by area, the dispersibility of the pigment is not satisfactory. For such reason, it is preferable that the hydroxyl value is in the above-described range, and the total amount of a diester, a triester, a tetraester, and a pentaester is preferably 10 to 100% by area.

Here, a monoester in the trehalose fatty acid esters has low dispersion ability, and further low solubility in oil. As a result, it has a problem in stability, such as precipitation of crystals over time. Furthermore, an octaester in which all the hydroxyl groups of the trehalose are esterified in the trehalose has low dispersion ability. For this reason, the amount of a monoester in the trehalose fatty acid esters is preferably less than 45% by area, and more preferably 25% by area or less. Furthermore, the amount of an octaester is preferably less than 70% by area, and more preferably 50% by area or less. On the other hand, a diester, a triester, a tetraester, a pentaester, a hexaester, and a heptaester have excellent dispersion ability, as compared to a typically used pigment dispersant. Among these, a diester, a triester, a tetraester, and a pentaester have more excellent dispersion ability, and a diester, a triester, and a tetraester have particularly more excellent dispersion ability.

Therefore, if it is required for the trehalose fatty acid ester composition of the present invention to have higher dispersion ability as a pigment dispersant, it is preferable that the hydroxyl value be 20 to 500, and the total amount of a diester, a triester, a tetraester, and a pentaester in the composition be 10 to 100% by area; it is more preferable that the hydroxyl value be 50 to 400, and the total amount of a diester, a triester, a tetraester, and a pentaester in the composition be 25 to 100% by area; and it is particularly more preferable that the hydroxyl value be 200 to 400, and the total amount of a diester, a triester, a tetraester, and a pentaester in the composition be 77 to 95% by area.

Further, the total amount of the a diester, a triester, and a tetraester in the trehalose fatty acid ester is preferably 2 to 100% by area, more preferably 10 to 100% by area, and particularly more preferably 60 to 85% by area.

Furthermore, among the trehalose fatty acid ester compositions, the trehalose fatty acid ester composition having the hydroxyl value of the trehalose fatty acid ester composition of the present invention of 100 to 500, is in any of the highly viscous state through the solid state, even in the case of using branched saturated fatty acid. For this reason, for example, if the composition is blended into a large amount in a cosmetic, the cosmetic feels slightly heavy upon use, or crystals may be precipitated over time. Accordingly, if the trehalose fatty acid ester composition of the present invention is blended as a base oil having excellent dispersibility in a large amount into a cosmetic, for the purpose of obtaining a dispersant having satisfactory dispersibility, sense of use, and solubility in oil, it is preferable that the hydroxyl value be 20 or more and less than 100, and the total amount of a diester, a triester, a tetraester, and a pentaester in the composition be 10 to 65% by area; it is more preferable that the hydroxyl value be 40 or more and less than 100, and the total amount of a diester, a triester, a tetraester, and a pentaester in the composition be 15 to 65% by area; and it is particularly more preferable that the hydroxyl value be 50 or more and less than 100, and the total amount of a diester, a triester, a tetraester, and a pentaester in the composition be 25 to 65% by area. The reason why it is not preferable that the value be out of the above-described range, is that if the total amount of a diester, a triester, a tetraester, and a pentaester in the composition is less than 10% by area, sufficient dispersion ability cannot be obtained.

Further, among the trehalose fatty acid esters, a diester, a triester, and a tetraester have more excellent dispersion ability, and exhibit their effect even with the amount of the composition of 2% by area or more. For this reason, the total amount of a diester, a triester, and a tetraester is preferably 2 to 39% by area, more preferably 4 to 39% by area, and particularly preferably 9 to 35% by area.

For example, if the composition is blended into a cosmetic product, for the purpose of providing a cosmetic that is satisfactory in terms of color development, sense of use, make-up lasting, odor, stability over time, and productivity, the trehalose fatty acid ester composition having the amount of a diester, a triester, and a tetraester in the composition of 2 to 40% by area and the amount of a hexaester, a heptaester, and an octaester of 30 to 98% by area is valid. It is more preferable for the composition to have the amount of a diester, a triester, and a tetraester of 10 to 40% by area, and to have the amount of a hexaester, a heptaester, and an octaester of 30 to 90% by area, and it is particularly preferable for the composition to have the amount of a diester, a triester, and a tetraester of 20 to 40% by area, and to have the amount of a hexaester, a heptaester, and an octaester of 30 to 80% by area.

The reason why the amount should be in the above-described range is that a diester, a triester, and a tetraester are excellent as pigment dispersants, for example, are excellent particularly in extender dispersibility. Furthermore, a hexaester, a heptaester, and an octaester are preferred particularly in terms of productivity due to it high flowability, and when it is applied to the skin, it has good sense of use. For this reason, it imparts improved sense of use and excellent productivity without deteriorating the pigment dispersibility. For example, if they are blended into a cosmetic product, for the purpose of providing a cosmetic satisfactory in terms of color development, sense of use, make-up lasting, odor, stability over time, and productivity, it is preferable that the ratio be in the above-described range.

Although the trehalose fatty acid ester composition exhibiting the ratio composition can be obtained by esterification with addition of raw materials in a specific ratio, a composition obtained by mixing the trehalose fatty acid ester compositions prepared by a known method in a specific ratio is more preferable, since this makes it possible to easily provide a composition uniformly having the components of a diester, a triester, and a tetraester, having excellent dispersibility, and the components of a hexaester, a heptaester, and an octaester, having good productivity, and sense of use.

For example, in a method for obtaining a composition having improved sense of use, and excellent productivity without deteriorating the pigment dispersibility, by mixing the trehalose fatty acid ester composition prepared by a known method in a specific ratio, it is possible to obtain a desired composition by mixing a trehalose fatty acid ester composition having an amount of a diester, a triester, and a tetraester of 25 to 85% by area, and a trehalose fatty acid ester composition having an amount of a hexaester, a heptaester, and an octaester of 65 to 99% by area, in a mass ratio of 2/98 to 27/73.

Furthermore, a single diester has excellent dispersion ability, but high crystallinity, and accordingly, when blended into a cosmetic, it is difficult to provide a cosmetic that is satisfactory in terms of shape retaining ability without generation of crystals over time, etc. However, since such a single diester has high solubility in a triester through a heptaester, it can be blended with these esters to improve usability or sense of use. For example, if it is blended into a cosmetic product, it is possible to obtain a cosmetic that is satisfactory in terms of color development, sense of use, make-up lasting, odor, and stability over time.

It is possible to obtain a desired composition, for example, by subjecting a trehalose fatty acid ester composition prepared by a known method to silica gel column chromatography, etc., and mixing the isolated trehalose difatty acid ester and the trehalose fatty acid ester composition having an amount of a triester through a heptaester of 20 to 90% by area, in a mass ratio of 2/98 to 27/73.

Further, among the trehalose fatty acid ester compositions of the present invention, the trehalose fatty acid ester composition having a hydroxyl value of 100 to 500, and the total amount of a diester, a triester, and a tetraester in the composition of 35 to 100% by area, can be used in combination with a polar oil having the remaining free hydroxyl groups, to impart improved usability or sense of use without deteriorating the pigment dispersibility, and when it can be blended in, for example, a cosmetic product, it is possible to obtain a cosmetic that is satisfactory in terms of color development, sense of use, make-up lasting, odor, and stability over time. The trehalose fatty acid ester composition of the present invention, for which, for example, a branched saturated fatty acid is used, preferably has a low hydroxyl value to avoid too high of a viscosity at room temperature, and better flowability in terms of productivity, etc., and tends to maintain dispersibility and solubility in oil, stability over time, and preferably to have a high hydroxyl value to give better dispersibility.

The trehalose fatty acid ester composition of the present invention has high dispersion ability, and thus is suitable as a dispersant for a pigment, etc., in particular, as a pigment dispersant to be blended into a cosmetic. Accordingly, for example, if it is used for a variety of cosmetics, a larger amount of the pigment can be blended into cosmetics, thereby providing cosmetics having excellent color tone. In particular, since it has excellent pigment dispersibility in the oily components, it is suitable for use in an oily cosmetic.

Moreover, since it can provide a cosmetic that has excellent sense of use, make-up lasting, odor, and stability over time, it is suitable for providing a cosmetic having a desired color tone of high quality.

For example, the trehalose fatty acid ester composition that has a hydroxyl value of 200 to 500, and the total amount of a diester, a triester, a tetraester in the composition of 60 to 100% by area, has high dispersion ability and very high viscosity, and thus if it is used as a powder binder for surface treatment of the powders containing an extender in an amount of 5% by mass or less, it can provide powders having high dispersibility, good sense of use, excellent absorptivity on the skin, long make-up lasting, and excellent shape-retaining ability.

Furthermore, since the trehalose fatty acid ester composition of the present invention has hardness enhancing action, it can be combined with a wax (oil gelling agent) such as a candelilla wax, a polyethylene wax, and a ceresine wax, to enhance the hardness and improve the shape-retaining ability, as compared with those with general oils. Among these, the candelilla wax can impart a higher hardness enhancing effect. For this reason, by blending the composition into a cosmetic, an amount of a wax to be used can be reduced, and larger amounts of other components can be blended therein. As a result, various cosmetics can be obtained. Furthermore, the cosmetic can also have good sense of use.

Therefore, the composition is suitably used in combination with a wax as a hardness enhancing agent.

In addition, the trehalose fatty acid ester composition of the present invention can be used as an oil or emulsifier due to its excellent characteristics as described above, in addition to a pigment dispersant, a hardness enhancing agent, and a powder binder, and also as a compounding agent for paints, inks, pencils, memory materials, lubricants, etc., in addition to cosmetics.

Examples of the cosmetics, into which the trehalose fatty acid ester composition of the present invention is preferably blended, include a make-up cosmetic, a milky lotion, a lotion, a washing cosmetic, an UV screening cosmetic, and a hair cosmetic. Specific examples thereof include a stick rouge, a gel rouge, a powder foundation, a liquid foundation, a stick concealer, a lip gloss, an eye-color pencil, an eye cream, a cleansing oil, a cleansing foam, a W/O type UV cream, a W/O type whitening cream, a clay wax, and a nail polish. Among these, the composition is preferably blended into oily cosmetics.

Further, an amount of the composition to be blended into the cosmetics is preferably 0.3 to 80% by mass, more preferably 1 to 65% by mass, and particularly preferably 2 to 55% by mass.

When the trehalose fatty acid ester composition of the present invention is used in these applications, various conventionally known components other than the composition may be blended in an appropriate amount according to the purpose, within the range that does not deteriorate the effects of the present invention. Hereinbelow, by way of examples, the cosmetics will be described in detail.

A cosmetic containing the trehalose fatty acid ester compositions of the present invention can be produced in accordance with a conventionally known method, by blending with various components usually used in the cosmetics within the range that does not deteriorate the effects of the present invention, if necessary.

For example, it is possible to arbitrarily blend anion surfactants, cation surfactants, ampholytic surfactants, lipophilic nonionic surfactants, hydrophilic nonionic surfactants, silicone surfactants, natural surfactants, liquid fats and oils, solid fats and oils, waxes, hydrocarbon oils, higher fatty acids, higher alcohols, ester oils, silicon oils, powders, moisturizers, natural water-soluble polymers, semisynthetic water-soluble polymers, synthetic water-soluble polymers, inorganic water-soluble polymers, thickeners, ultraviolet absorbers, metal ion sequesters, lower alcohols, polyalcohols, monosaccharides, oligosaccharides, polysaccharides, amino acids, organic amines, synthetic-resin emulsions, pH adjuster, vitamins, antioxidants, antioxidizing auxiliaries, fragrances and water, if necessary.

Examples of the anion surfactants include fatty-acid soaps such as substrates for soap, sodium laurate and sodium palmitate; salts of higher alkyl sulfuric ester such as sodium lauryl sulfate and potassium lauryl sulfate; salts of alkyl ether sulfuric ester such as POE-triethanolamine lauryl sulfate and POE-sodium lauryl sulfate; N-acylsarcosine acids such as sodium lauroyl sarcosine; higher fatty acid amide sulfonates such as sodium N-myristoyl-N-methyl taurate, sodium palm oil fatty acid methyl ester tauride and sodium lauryl methyl tauride; salts of phosphoric ester such as sodium POE-oleyl ether phosphate and POE-stearyl ether phosphoric acid; sulfosuccinates such as sodium di-2-ethylhexyl sulfosuccinate, sodium monolauroyl monoethanolamide polyoxyethylene sulfosuccinate and sodium lauryl polypropylene glycol sulfosuccinate; alkylbenzene sulfonates such as linear sodium dodecylbenzenesulfonate, linear triethanolamine dodecylbenzenesulfonate and linear dodecylbenzenesulfonic acid; N-acylglutamates such as monosodium N-lauroyl glutamate, disodium N-stearoyl glutamate and monosodium N-myristoyl-L-glutamate; higher fatty acid ester sulfates such as hardened palm oil fatty acid glycerin sodium sulfate; sulfated oils such as sulfated caster oil; POE-alkylether carboxylic acids; POE-alkylallyl ether carboxylates; α-olefin sulfonates; higher fatty acid ester sulfonates; secondary alcohol sulfates; higher fatty acid alkylol amide sulfates; sodium lauroyl monoethanolamide succinates; ditriethanolamine N-palmitoyl aspartate; and casein sodium.

Examples of the cation surfactants include alkyl trimethyl ammonium salts such as stearyl trimethyl ammonium chloride and lauryl trimethyl ammonium chloride; alkylpyridinium salts such as distearyl dimethyl ammonium chloride dialkyl dimethyl ammonium salts, poly(N,N'-dimethyl-3,5-methylene piperidinium) chloride and cetylpyridinium chloride; alkyl quaternary ammonium salts, alkyl dimethyl benzyl ammonium salts, alkyl isoquinolinium salts, dialkyl morphonium salts, POE-alkylamine, alkylamine salts, polyamine fatty acid derivatives, amyl alcohol fatty acid derivatives, benzalkonium chloride and benzetonium chloride.

Examples of the ampholytic surfactants include imidazoline ampholytic surfactants such as sodium 2-undecyl-N,N,N-(hydroxyethyl carboxymethyl)-2-imidazoline and salts of disodium 2-cocoyl-2-imidazolinium hydroxide-1-carboxyethyloxy; and betaine ampholytic surfactants such as 2-heptadecyl-N-carboxymethyl-N-hydroxyethyl imidazolinium betaine, lauryl dimethylamino acetic acid betaine, alkyl betaine, amido betaine and sulfobetaine.

Examples of the lipophilic nonionic surfactants include sorbitan fatty acid esters such as sorbitan monooleate, sorbitan monoisostearate, sorbitan monolaurate, sorbitan monopalmitate, sorbitan monostearate, sorbitan sesquioleate, sorbitan trioleate, diglycerol sorbitan penta-2-ethylhexylate and tetra-2-ethylhexyl diglycerol sorbitan; glycerin fatty acids such as mono cottonseed oil fatty acid glycerin, monoerucic acid glycerin, sesquioleic acid glycerin, monostearic acid glycerin, α,α'-oleic acid pyroglutamic acid glycerin and monostearic acid glycerin; polyglycerin fatty acid esters such as diglyceryl monoisostearate and diglyceryl diisostearate; propylene glycol fatty acid esters such as propylene glycol monostearate; hardened castor oil derivatives; and glycerin alkylethers.

Examples of the hydrophilic nonionic surfactants include POE-sorbitan fatty acid esters such as POE-sorbitan monooleate, POE-sorbitan monostearate, POE-sorbitan monooleate and POE-sorbitan tetraoleate; POE-sorbit fatty acid esters such as POE-sorbit monolaurate, POE-sorbit monooleate, POE-sorbit pentaoleate, POE-sorbit monostearate; POE-glycerin fatty acid esters such as POE-glycerin monostearate, POE-glycerin monoisostearate and POE-glycerin triisostearate; POE-fatty acid esters such as POE-monooleate, POE-distearate, POE-monodioleate and distearic acid ethylene glycol; POE-alkylethers such as POE-laurylether, POE-oleylether, POE-stearylether, POE-behenylether, POE-2-octyldodecylether and POE-cholestanolether; pluronic types such as pluronic; POE-POP-alkylethers such as POE-POP-cetylether, POE-POP-2-decyltetradecylether, POE POP-monobutylether, POE•POP-hydrogenated lanolin and POE•POP-glycerinether; tetra-POE.tetra-POP-ethylenediamine condensation products such as tetronic; POE-castor oil hardened castor oil derivatives such as POE-castor oil, POE-hardened castor oil, POE-hardened castor oil monoisostearate, POE-hardened castor oil triisostearate, POE-hardened castor oil monopyroglutamic acid monoisostearic acid diester and POE-hardened castor oil maleic acid; POE-beeswax-lanolin derivatives such as POE-sorbit beeswax; alkanolamides such as palm oil fatty acid diethanolamide, monoethanolamide laurate and fatty acid isopropanolamide; POE-propylene glycol fatty acid esters; POE-alkylamines; POE-fatty acid amides; sucrose fatty acid esters; POE-nonylphenyl formaldehyde condensation products; alkylethoxy dimethyl amine oxides and trioleyl phosphoric acids.

Examples of the silicone surfactants include polyether-modified polysiloxane, a polyoxyalkylene alkylmethyl polysiloxane-methyl polysiloxane copolymer, and alkoxy modified polysiloxane.

Examples of the natural surfactants include lecithins such as soybean phospholipids, hydrogenated soybean phospholipids, egg yolk phospholipids and hydrogenated egg yolk phospholipids; and soybean saponins.

Examples of the liquid fats and oils include avocado oil, camellia oil, turtle oil, macadamia nut oil, corn oil, sunflower oil, mink oil, olive oil, canola oil, egg yolk oil, sesame seed oil, persic oil, wheat germ oil, sasanqua oil, castor oil, linseed oil, safflower oil, grapeseed oil, cottonseed oil, perilla oil, soybean oil, earthnut oil, tea seed oil, torreya seed oil, rice bran oil, aleurites fordii oil, Japanese tung oil, jojoba oil, germ oil, evening primrose oil, trioctanoic acid glycerin and triisopalmitic acid glycerin. Here, the liquid fats and oils mean liquid fats and oils at room temperature.

Examples of the solid fats and oils include cacao butter, palm oil, beef tallow, mutton tallow, horse fat, palm kernel oil, lard, beef bone fat, tree wax kernel oil, hoof oil, tree wax, hardened palm oil, hardened palm oil, hardened beef tallow, hardened oil and hardened castor oil Examples of the waxes include beeswax, candelilla wax, cotton wax, carnauba wax, bayberry wax, Ibota wax, whale wax, montan wax, rice bran wax, kapok wax, sugarcane wax, lanolin, acetylated lanolin, liquid lanolin, isopropyl lanolate, reduced lanolin, hard lanolin, hexyl laurate, jojoba wax, shellac wax, POE lanolin alcohol ether, POE lanolin alcohol acetate, POE cholesterol ether, lanolin fatty acid polyethylene glycol and POE hydrogenated lanolin alcohol ether.

Examples of the hydrocarbon oils include liquid paraffin, isoparaffin, heavy liquid isoparaffin, paraffin, ozocerite, squalane, vegetable squalane, pristine, ceresin, squalene, vaseline, microcrystalline wax, paraffin wax, montan wax, olefin oligomer, polyisobutylene, polybutene and hydrogenated polybutene.

Examples of the higher fatty acids include lauric acid, myristic acid, palmitic acid, stearic acid, behenic acid, oleic acid, undecylenic acid, tall oil acid, isostearic acid, linoleic acid, linolenic acid, eicosapentaenoic acid (EPA) and docosahexaenoic acid (DHA).

Examples of higher alcohols include linear alcohols such as lauryl alcohol, cetyl alcohol, stearyl alcohol, behenyl alcohol, myristyl alcohol, oleyl alcohol, setostearyl alcohol; and branched alcohols such as monostearyl glycerin ether (batyl alcohol), 2-decyl tetradecynol, lanolin alcohol, cholesterol, phytosterol, hexyl dodecanol, isostearic alcohol and octyl dodecanol.

Examples of the ester oils include isopropyl myristate, cetyl isooctanoate, octyldodecyl myristate, isopropyl palmitate, isooctyl palmitate, butyl stearate, hexyl laurate, myristyl myristate, decyl oleate, hexyldecyl dimethyl octanoate, cetyl lactate, myristyl lactate, octyldodecyl lactate, acetylated lanolin, isocetyl stearate, isocetyl isostearate, cholesteryl 12-hydroxy stearate, phytosteryl 12-hydroxy stearate, phytosteryl oleate, ethylene glycol di-2-ethylhexanoate, propylene glycol dicaprate, dipentaerythritol fatty acid ester, N-alkyl glycol monoisostearate, neopentyl glycol dicaprate, diisostearyl malate, glycerin di-2-heptyl undecanoate, trimethylolpropane tri-2-ethylhexanoate, trimethylolpropane triisostearate, pentaerythritol tetra-2-ethylhexanoate, glyceryl tri-2-ethylhexanoate, tri(capryl/capric acid) glyceryl ester, tri (capryl/caprin/myristin/stearic acid) glyceride, trimethylolpropane triisostearate, cetyl 2-ethylhexanoate, 2-ethylhexylpalmitate, glycerin trimyristate, tri-2-heptyl undecanoic acid glyceride, polyglyceryl diisostearate, polyglyceryl triisostearate, polyglyceryl tetraisostearate, diglyceryl triisostearate, diglyceryl tetraisostearate, erythrityl tri-2-ethylhexanoate, ditrimethylolpropane tri-2-ethylhexanoate, (isostearic acid/sebacic acid) ditrimethylolpropane oligoester, castor oil fatty acid methyl ester, oleyl oleate, acetoglyceride, 2-heptyl undecyl palmitate, diisobutyl adipate, (adipic acid/2-ethylhexanoic acid/stearic acid) glycerin oligoester, (2-hexyl decanoic acid/sebacic acid) diglyceryl oligoester, N-lauroyl-L-glutamic acid-2-octyldodecylester, di-2-heptyl undecyl adipate, ethyl laurate, di-2-ethylhexyl sebacate, 2-hexyldecyl myristate, 2-hexyldecyl palmitate, 2-hexyldecyl adipate, diisopropyl sebacate, 2-ethylhexyl succinate, ethyl acetate, butyl acetate and triethyl citrate.

Examples of the silicon oils include chain polysiloxanes such as dimethyl polysiloxane, methylphenyl polysiloxane and methylhydrogen polysiloxane; cyclic polysiloxanes such as octamethylcyclotetrasiloxane, decamethylcyclopentasiloxane, dodecamethyl-cyclohexasiloxane and tetrahydrotetramethylcyclotetrasiloxane; and polyoxyethylene polyalkyl siloxane.

Usability of the cosmetics containing the trehalose fatty acid ester composition of the present invention can be improved and the toning of the cosmetics can be adjusted by adding powders. Furthermore, the powders that can be used are not particularly limited by forms, such as spherical, plate and needle shapes; particle sizes such as fumy particles, fine particles and pigments; and particle structures such as porous and non-porous structures, and inorganic powders, photoluminescent powders, organic powders, pigment powders, metal powders and composite powders can be used. Specific examples of the powders include white inorganic pigments such as titanium oxide, zinc oxide, cerium oxide and barium sulfate; colored inorganic pigments such as ferric oxide, titanic iron, (-ferric oxide, iron oxide yellow, iron oxide black, carbon black, low-dimensional titanic oxide, chrome oxide, chromium hydroxide, iron blue, cobalt blue, yellow ocher, mango violet, cobalt violet and titanic cobalt; organic pigment powders such as Red No. 201, Red No. 202, Red No. 205, Red No. 220, Red No. 226, Red No. 228, Red No. 405, Orange No. 203, Orange No. 204, Blue No. 404, Yellow No. 205 and Yellow No. 401; organic pigment powders such as zirconium, barium and aluminum lake, e.g., Red No. 3, Red No. 104, Red No. 106, Red No. 227, Red No. 230, Red No. 401, Red No. 505, Orange No. 205, Yellow No. 4, Yellow No. 5, Yellow No. 202, Yellow No. 203, Green No. 3 and Blue No. 1. Further, examples of the extenders include white extenders such as talc, mica, white mica, gold mica, red mica, black mica, synthesized mica, sericite, lithia mica, vermiculite, synthesized sericite, kaolin, silicon carbide, bentonite, smectite, aluminum oxide, magnesium oxide, zirconium oxide, antimony oxide, diatom earth, aluminum silicate, magnesium aluminum metasilicate, calcium silicate, barium silicate, magnesium silicate, strontium silicate, metal salts of tungsten acid, calcium phosphate, calcium carbonate, magnesium carbonate, calcined calcium sulfate, apatite fluoride, hydroxyapatite, silica, zeolite, ceramic powder and boron nitride; photoluminescent powders such as titanium dioxide coated mica, titanium dioxide coated talc, titanium dioxide coated bismuth oxychloride, colored titanium oxide coated mica, ferric oxide mica titanium, iron blue treated mica titanium, carmine treated mica titanium, bismuth oxychloride, argentine, polyethylene telephthalate/aluminum/epoxy laminated powder and polyethylene telephthalate/polyolefin laminated powder; copolymer resins such as polyamide resins, polyethylene resins, polyacryl resins, polyester resins, fluorine resins, cellulose resins, polystyrene resins and styrene-acryl copolymer resins; organic polymer resin powders such as polypropylene resins, silicon resins, urethane resins, benzoguanamine resins and polyethylene tetrafluoride resins; organic low molecular powders such as zinc myristate, zinc stearate, calcium palmitate, aluminum stearate and N-acyllysine; natural organic powders such as starch, silk powder and cellulose powder; or metal powders such as aluminum powder, magnesium powder, copper powder, gold powder and silver powder; and compound powders such as particulate titanium oxide coated mica titanium, particulate zinc oxide coated mica titanium, barium sulfate coated mica titanium, silicon dioxide containing titanium oxide and silicon dioxide containing zinc oxide. These powders can be used alone, or in a combination of two or more kinds thereof, and a complex compound(s) thereof can also be used. These powders can be used, of which the surface is treated by using one or more kinds selected from fluorine compounds, silicon compounds, metal soaps, lecithins, hydrogenated lecithins, collagen, hydrocarbons, higher fatty acids, higher alcohols, esters, waxes, and surfactants.

Examples of the moisturizers include polyethylene glycol, propylene glycol, glucerine, 1,3-butylene glycol, xylitol, sorbitol, maltitol, chondroitin sulfuric acid, hyaluronic acid, mucoitinsulfuric acid, Trichosanthis Semen acid, atelocollagen, cholesteryl-12-hydroxy stearate, sodium lactate, urea, bile salt, dl-pyrrolidone carboxylate, short-chain soluble collagen, diglycerin (EO) PO adducts, rosa roxburghii, yarrow extracts and melilot extracts.

Examples of the natural water-soluble polymers include plant polymers such as gum arabic, gum tragacanth, galactan, guar gum, gum carob, Karaya gum, carrageenan, pectin, agar, quince seed (marmelo), algae colloid (brown algae extracts) and starch (rice, corn, potato, wheat); microbial polymers such as xanthan gum, dextran, succinoglucan and pullulan; and animal polymers such as collagen, casein, albumin and gelatin.

Examples of the semisynthetic water-soluble polymers include starch polymers such as carboxymethyl starch and methylhydroxypropyl starch; cellulose polymers such as methyl cellulose, nitrocellulose, methylhydroxypropyl cellulose, cellulose sodium sulfate, hydroxypropyl cellulose, carboxymethyl cellulose, sodium carboxymethyl cellulose, crystalline cellulose and cellulose powder; and alginic acid polymers such as sodium alginate and alginic acid propylene glycol ester.

Examples of the synthetic water-soluble polymers include vinyl polymers such as polyvinyl alcohol, polyvinyl methyl ether, polyvinyl pyrrolidone and carboxyvinyl polymer (carbopol); polyoxyethylene polymers such as polyethylene glycol 20,000, 40,000, and 60,000; acrylic polymers such as polyoxyethylene polyoxypropylene copolymer copolymerized polymer, polyacrylic acid sodium, polyethyl acrylate and polyacrylamide; and polyethylene imine and cation polymer.

Examples of the inorganic water-soluble polymers include bentonite, AlMg silicate (bee gum), laponite, hectorite and anhydrous silicic acid.

Examples of the thickeners include gum arabic, carrageenan, Karaya gum, gum tragacanth, carob gum, quince seed (marmelo), casein, dextrin, gelatin, sodium pectin acid, sodium alginate, methylcellulose, ethylcellulose, CMC, hydroxyethyl cellulose, hydroxypropyl cellulose, PVA, PVM, PVP, sodium polyacrylate, carboxyvinyl polymer, locust bean gum, guar gum, tamarind gum, dialkyl dimethyl ammonium cellulose sulfate, xanthan gum, magnesium aluminum silicate, bentonite and hectorite.

Examples of the ultraviolet absorbers include benzoic acid ultraviolet absorbers such as para-aminobenzoic acid (hereinafter abbreviated as PABA), PABA mono glycerin ester, N,N-dipropoxy PABA ethyl ester, N,N-diethoxy PABA ethyl ester, N,N-dimethyl PABA ethyl ester, N,N-dimethyl PABA butyl ester and N,N-dimethyl PABA ethyl ester; anthranilic acid ultraviolet absorbers such as homomethyl-N-acetylanthranilate; salicylic acid ultraviolet absorbers such as amyl salicylate, menthyl salicylate, homomethyl salicylate, octyl salicylate, phenyl salicylate, benzyl salicylate and p-isopropanol phenyl salicylate; cinnamic acid ultraviolet absorbers such as octyl cinnamate, ethyl-4-isopropyl cinnamate, methyl-2,5-diisopropyl cinnamate, ethyl-2,4-diisopropyl cinnamate, methyl-2,4-diisopropyl cinnamate, propyl-p-methoxycinnamate, isopropyl-p-methoxycinnamate, isoamyl-p-methoxycinnamate, octyl-p-methoxycinnamate (2-ethylhexyl-p-methoxycinnamate), 2-ethoxyethyl-p-methoxycinnamate, cyclohexyl-p-methoxycinnamate, ethyl-α-cyano-β-phenyl cinnamate, 2-ethylhexyl-α-cyano-β-phenyl cinnamate and glyceryl mono-2-ethylhexanoyl-diparamethoxycinnamate; benzophenone ultraviolet absorbers such as 2,4-dihydroxybenzophenone, 2,2'-dihydroxy-4-methoxybenzophenone, 2,2'-dihydroxy-4,4'-dimethoxybenzophenone, 2,2',4,4'-tetrahydroxybenzophenone, 2-hydroxy-4-methoxybenzophenone, 2-hydroxy-4-methoxy-4'-methylbenzophenone, 2-hydroxy-4-methoxybenzophenone-5-sulfonate, 4-phenylbenzophenone, 2-ethylhexyl-4'-phenylbenzophenone-2-carboxylate, 2-hydroxy-4-n-octoxybenzophenone and 4-hydroxy-3-carboxybenzophenone; 3-(4'-methylbenzylidene)d,l-camphor; 3-benzyhdene-d,l-camphor; urocanic acid, urocanic acid ethyl ester; 2-phenyl-5-methylbenzoxazole; 2,2'-hydroxy-5-methylphenyl benzotriazole; 2-(2'-hydroxy-5'-t-octylphenyl) benzotriazole; 2-(2'-hydroxy-5'-methylphenyl) benzotriazole; dibenzalazine; dianisoylmethane; 4-methoxy-4'-t-butyl dibenzoylmethane; 5-(3,3-dimethyl-2-norbornylidene)-3-pentane-2-one; and 2,4,6-trianilino-p-(carbo-2'-ethylhexyl-1'-oxy) 1,3,5-triazine.

Examples of the metal ion sequestrants include 1-hydroxyethane-1,1-diphosphonate, tetrasodium salt of 1-hydroxyethane-1,1-diphosphonate, disodium edentate, edetate trisodium, edentate tetrasodium, sodium citrate, sodium polyphosphate, sodium metaphosphate, gluconic acid, phosphoric acid, citric acid, ascorbic acid, succinic acid, edetic acid, and trisodium ethylenediamine hydroxyethyl triacetate.

Examples of the lower alcohols include methanol, ethanol, propanol, isopropanol, isobutyl alcohol and t-butyl alcohol.

Examples of the polyalcohols include dihydric alcohols such as ethylene glycol, propylene glycol, trimethylene glycol, 1,2-butylene glycol, 1,3-butylene glycol, tetramethylene glucol, 2,3-butylene glucol, pentamethylene glucol, 2-butene-1,4-diol, hexylene glycol and octylene glycol; trihydric alcohols such as glycerin, trimethylolpropane and 1,2,6-hexanetriol; tetrahydric alcohols such as pentaerythritol; pentahydric alcohols such as xylitol; hexahydric alcohols such as sorbitol and mannitol; polyalcohol polymers such as diethylene glycol, dipropylene glycol, triethylene glucol, polypropylene glycol, tetraethylene glycol, diglycerin, polyethylene glycol, triglycerin, tetraglycerin and polyglycerin; dihydric alcoholic alkyl ethers such as ethylene glycol monomethyl ether, ethylene glucol monoethyl ether, ethylene glycol monobutyl ether, ethylene glycol monophenyl ether, ethylene glycol monohexyl ether, ethylene glycol mono 2-methylhexyl ether, ethylene glycol isoamyl ether, ethylene glycol benzyl ether, ethylene glycol isopropyl ether, ethylene glycol dimethyl ether, ethylene glycol diethyl ether and ethylene glycol dibutyl ether; dihydric alcohol alkyl ethers such as diethylene glycol monomethyl ether, diethylene glucol monoethyl ether, diethylene glycol monobutyl ether, diethylene glycol dimethyl ether, diethylene glycol diethyl ether, diethylene glycol butyl ether, diethylene glycol methylethyl ether, triethylene glycol monomethyl ether, triethylene glycol monoethyl ether, propylene glycol monomethyl ether, propylene glycol monoethyl ether, propylene glycol monobutyl ether, propylene glycol isopropyl ether, dipropylene glycol methyl ether, dipropylene glycol ethyl ether and dipropylene glycol butyl ether; dihydric alcohol ether esters such as ethylene glycol monomethyl ether acetate, ethylene glycol monoethyl ether acetate, ethylene glycol monobutyl ether acetate, ethylene glycol monophenyl ether acetate, ethylene glycol diadipate, ethylene glycol disuccinate, diethylene glycol monoethyl ether acetate, diethylene glycol monobutyl ether acetate, propylene glycol monomethyl ether acetate, propylene glycol monoethyl ether acetate, propylene glycol monopropyl ether acetate and propylene glycol monophenyl ether acetate; glycerin monoalkyl ethers such as xyl alcohol, selachyl alcohol and batyl alcohol; sugar alcohols such as sorbitol, maltitol, maltotriose, mannitol, lactitol, sucrose, erythritol, glucose, fructose, amylolytic sugar, maltose, xylitose and, amylolytic sugar reducing alcohol; glysolid; tetrahydroflufuryl alcohol; POE-tetrahydroflufuryl alcohol; POP-butyl ether; POP/POE-butyl ether; tripolyoxy propylene glycerin ether; POP-glycerin ether; POP-glycerin ether phosphoric acid; and POP/POE-pentane erythritol ether.

Examples of the monosaccharides include trioses such as D-glyceryl aldehyde and dihydroxy acetone; tetroses such as D-erythrose, D-erythrulose, D-threose and erythritol; pentoses such as L-arabinose, D-xylose, L-lyxose, D-arabinose, D-ribose, D-ribulose, D-xylulose and L-xylulose; hexoses such as D-glucose, D-talose, D-psicose, D-galactose, D-fructose, L-galactose, L-mannose, and D-tagatose; heptoses such as aldoheptose and heptrose; octoses such as octrose; deoxy sugars such as 2-deoxy-D-ribose, 6-deoxy-L-galactose and 6-deoxy-L-mannose; amino sugars such as D-glucosamine, D-galactosamine, sialic acid, amino uronic acid, and muramic acid; and uronic acids such as D-glucuronic acid, D-mannuronic acid, L-guluronic acid, D-galacturonic acid, and L-iduronic acid.

Examples of the oligosaccharides include sucrose, gunchianose, umbelliferose, lactose, planteose, isolignoses, α,α-trehalose, raffinose, lignoses, umbilicine, and stachyose verbascoses.

Examples of the polysaccharides include cellulose, quince seed, chondroitin sulfuric acid, starch, dextrin, glucomannan, chitin, galactan, dermatan sulfuric acid, glycogen, gum arabic, heparin sulfuric acid, hyaluronic acid, gum tragacanth, keratan sulfuric acid, chondroitin, xanthan gum, mucoitinsulfuric acid, guar gum, dextran, keratosulfuric acid, locust bean gum, succinoglucan, and caronin acid.

Examples of the amino acids include neutral amino acids such as threonine and cysteine; and basic amino acids such as hydroxylysine. Further, amino acid derivatives include sodium acylsarcosine (sodium lauroylsarcosine), acyl glutamate, acyl (-alanine sodium, glutathione, and pyrrolidone carboxylic acid.

Examples of the organic amines include monoethanolamine, diethanolamine, triethanolamine, morpholine, triisopropanolamine, 2-amino-2-methyl-1,3-propanediol and 2-amino-2-methyl-1-propanol.

Examples of the synthetic resin emulsions include an acrylic resin emulsion, a polyacrylic acid ethyl emulsion, an acrylic resin solution, a polyacryl alkyl ester emulsion and a polyvinyl acetate resin emulsion.

Examples of the pH adjusters include buffers such as lactic acid-sodium lactate and citric acid-sodium citrate.

Examples of the vitamins include vitamin A, vitamin B1, vitamin B2, vitamin B6, vitamin C and derivatives thereof, vitamin E, vitamin K and derivatives thereof; pantothenic acids and derivatives thereof; biotins, and the like.

Examples of the antioxidants include tocopherols, dibutyl hydroxytoluene, butylhydroxyanisol and gallic acid esters.

Examples of the antioxidizing auxiliaries include phosphoric acids, citric acids, ascorbic acids, maleic acids, malonic acids, succinic acids, fumaric acids, cephalin, hexametaphosphate, phytic acid and ethylenediamine tetraacetic acid.

Examples of the other components that can be blended into the cosmetic compositions include antiseptic agents such as ethylparaben and butylparaben; ultraviolet absorbers such as benzophenone derivatives, PABA derivatives, cinnamic acid derivatives, salicylic acid derivatives, 4-tert-butyl-4'-methoxydibenzoylmethane and oxybenzone; antiflash agents such as glycyrrhizinic acid derivatives, glycyrrhetinic acid derivatives, salicylic acid, derivatives, hinokitiol, zinc oxide and, allantoin; skin whitening agents such as placental extracts, vitamin C and derivatives thereof, hydroquinone and derivatives thereof, and saxifragaceous extracts; extracts of cork tree bark, coptis root, lithospermi radix, peony root, *swertia* herb, birch, sage, loquat, carrots, *aloe*, tree mallow, iris, grapes, *coix* seed, loofah, lily, saffron, Cnidium Rhizome, ginger, *hypericum*, ononis, garlic, *capsicum*, citrus unshiu peel, Japanese angelica root and seaweed; activator agents such as royal jelly, photosensitive pigments, cholesterol derivatives and infant blood extracts; blood circulation promoters such as 4-hydroxy-3-methoxybenzyl nonylic acid amide, nicotinic acid benzyl ester, nicotinic acid β-butoxy ethyl ester, capsaicin, gingerone, cantharides tincture, ichthammol, tannic acid, α-borneol, nicotinic acid tocopherol, inositol hexanicotinate, cyclandelate, cinnarizine, tolazoline, acetylcholine, verapamil, cepharanthine, γ-orizanol; antiseborrheic agents such as sulfur and thianthol; tranexamic acids; thiotaurine; and hypotaurine.

Besides, an oil gelling agent can be contained in the cosmetics of the present invention. The make-up cosmetics containing a trehalose fatty acid ester composition and an oil gelling agent are particularly excellent in sense of use, have good shape retaining ability and preservation stability thereof, and excellent usability.

The shape retaining ability and gelation ability of an oily cosmetic are synergistically improved by combining the trehalose fatty acid ester compositions of the present invention with the gelling agent, and effects thereof can be sufficiently exhibited. Even with a small amount of the gelling agent, sufficient gelation can be attained. As a result, usability is good and feeling of a cosmetic film is sustained, and therefore, a make-up cosmetic having excellent 1 make-up lasting can be obtained.

Here, the oil gelling agents in the present invention refer to those that can solidify or gelatinize oily components such as fats and oils, waxes, hydrocarbon oils, higher fatty acids, higher alcohols, ester oils and silicon oils, and a commercially available product thereof can be used.

Further, examples of the oil gelling agents include waxes, 12-hydroxystearic acid, dextrin fatty acid esters, sucrose fatty acid esters, metal soaps, anhydrous silicic acids, (behenic acid/eicosanic diacid) glyceryl and organic modified clay minerals. These may be used alone, or in combination of two or more kinds thereof.

Examples of the waxes that are the oil gelling agents include paraffin wax, ceresin wax, microcrystalline wax, Fischer-Tropsch wax, polyethylene wax, carnauba wax and candelilla wax. These may be used alone, or in combination of two or more kinds thereof.

Examples of the commercially available products thereof include trade name: Purified Carnauba Wax No. 1, manufactured by Noda Wax Co., Ltd.; trade name: OZOKERAITE WAX SP-273P, manufactured by STRAHL & PITSH INC.; trade name: Microwax 190Y, manufactured by Mobil Oil Co.; trade name: Himic 1080/2095, manufactured by Nippon Seiro Co., Ltd.; trade name: Sanwax E-200/E-300, manufactured by Sanyo Chemical Industries, Ltd.; trade name: Mobil 180, manufactured by Mobil Oil Co.; trade name: Starwax 100, produced by Bareco; trade name: Nisseki Microwax 180, manufactured by Nippon Oil Corporation; trade name: Fischer-Tropsch Wax FT-95/FT100H/FT-150/FT-200, manufactured by Sasol Wax Limited; trade name: BeSquare 180/185/190/195, manufactured by Bareco; trade name: Polywax 500/655, manufactured by Bareco; and trade name: Sasol Wax H1/C1/C2, manufactured by Sasol Wax Limited.

12-Hydroxystearic acid that is the oil gelling agent is a fatty acid having a hydroxyl group. For example, it can be obtained by hydrogenating a recinoleic acid that is obtained from castor oil.

Dextrin fatty acid esters that are the oil gelling agents are soluble in oil and ester compounds of a linear or branched, saturated or unsaturated fatty acids having 8 to 24 carbon atoms (preferably 14 to 18 carbon atoms) with a dextrin having average degree of polymerization of 10 to 50 (preferably 20 to 30).

Examples thereof include dextrin palmitic acid, palmitic acid/2-ethylhexanoic acid dextrin, dextrin stearic acid, palmitic acid/stearic acid dextrin, dextrin oleic acid, dextrin isopalmitic acid and dextrin isostearic acid. These may be used alone, or in combination of two or more kinds thereof.

Examples of the commercially available products of dextrin palmitic acid include trade name: Leopal KL, manufactured by Chiba Seifun Co., Ltd. and trade name: Leopal TL, manufactured by Chiba Seifun Co., Ltd. Further, the commercially available products of palmitic acid/2-ethylhexanoic acid dextrin include trade name: Leopal TT, manufactured by Chiba Seifun Co., Ltd.

As the sucrose fatty acid esters that are the oil gelling agents, any sucrose fatty acid esters that are usually used in the cosmetic compositions can be used, and it is particularly preferable to use fatty acid esters of palmitic acid, stearic acid, behenic acid, oleic acid and lauric acid.

Examples of the metal soaps that are the oil gelling agents include isostearic acid aluminium, stearic acid aluminium and stearic acid calcium, and these may be used alone, or in combination of two or more kinds thereof.

As for anhydrous silicic acids that are the oil gelling agents, if they are those that are usually used in the cosmetic compositions, any forms of fumy, porous, non porous, and spherical ones can be used. It is possible to use one or more kinds selected from the above. It is particularly preferable to use a fumy anhydrous silicic acid or a hydrophobized fumy anhydrous silicic acid that are obtained by treating fumy anhydrous silicic acid with hydrophobizing treatment.

In addition, a primary particle size of the fumy anhydrous silicic acid or hydrophobized fumy anhydrous silicic acid is preferably 50 nm or less, and particularly preferably 20 nm or less. The fumy anhydrous silicic acid can be obtained by hydrolyzing silicon tetrachloride in hydrogen and enzymatic salts.

Examples of the commercially available products of the anhydrous silicic acid include Aerosil 50, Aerosil 130, Aerosil 200, Aerosil 200V, Aerosil 200CF, Aerosil 200FAD, Aerosil 300, Aerosil 300CF and Aerosil 380, all manufactured by Nippon Aerosil Co., Ltd.

Examples of the methods for hydrophobizing the fumy anhydrous silicic acid include trimethylsiloxy treatment with trimethyl chlorosialane and hexamethyldisilazane, octyl silanization, coating and baking using methylhydrogen polysiloxane, and coating with metal soaps.

Examples of the commercially available products of the hydrophobized fumy anhydrous silicic acid include Aerosil R-972, Aerosil R-972V, Aerosil R-972CF, Aerosil R-974, Aerosil R-976S, Aerosil RX200, Aerosil RY200, Aerosil R-202, Aerosil R-805, Aerosil R-812, and Aerosil RA200H, all manufactured by Nippon Aerosil Co., Ltd.; Taranox 500 manufactured by Talco Co.; and CAB-O-SIL TS-530 manufactured by Cabot Corporation.

(Behenic acid/eicosanic diacid) glyceryl that is the oil gelling agent is an oligomer ester of behenic acid and eicosanic diacid with glycerin. Examples of the commercially available products thereof include trade name: Nomcort HK-G, by the Nisshin OilliO Group, Ltd.

Examples of the organic modified clay minerals that are the oil gelling agents include organic modified bentonites and those wherein water swell clay minerals are treated with quaternary ammonium salts. These may be used alone, or in combination of two or more kinds thereof.

Examples of the commercially available products of the organic modified bentonites include trade name: Bentone 38, manufactured by NL Industries, Inc. and trade name: Bentone 27, manufactured by NL Industries, Inc.

The cosmetics containing the trehalose fatty acid ester composition of the present invention can be prepared by using a conventionally known preparation method.

EXAMPLES

Hereinbelow, the present invention will be described in detail with reference to specific Examples, Further, the present invention should not be construed to be limited by the following Examples in any way.

As used herein, the content of the trehalose fatty acid ester refers to an area percentage (% by area), as determined by means of high-performance liquid chromatography analysis (hereinafter simply referred to as HPLC), that is analyzed and determined by the method as follows.

Method for Analysis and Measurement of the Composition of the Trehalose Fatty Acid Ester Compositions and the Comparative Sugar Fatty Acid Ester Compositions.

Analysis and measurement of the composition of the trehalose fatty acid ester compositions 1 to 9, and the comparative sugar fatty acid ester compositions 1 to 5 were conducted by means of HPLC, using an RI (differential refraction index) method, with reference to "Determination of Sucrose Fatty Acid Ester by High-performance Liquid Chromatography; J. Oleo Sci., Vol. 50, No. 4 (2001)".

For the separation of each component in the trehalose fatty acid ester compositions and comparative sugar fatty acid ester compositions, GPC columns and ODS columns were used together to separate the remaining raw materials, a monoester, a diester, a triester, and a tetra- or higher valent polyester in the analysis and measurement of the composition using the GPC columns (in the GPC columns, it is impossible to separate a tetraester through an octaester, individually, thus a polyester is separated collectively), to obtain the composition ratio for each of the components. Further, in the analysis and measurement of the composition using the ODS column, a tetraester, a pentaester, a hexaester, a heptaester, and an octaester are separated, to obtain each composition ratio. From the composition ratio of a tetra- or higher valent polyester, as determined using the GPC columns, the composition ratios of a tetraester, a pentaester, a hexaester, a heptaester, and an octaester were determined by conversion. Hereinbelow, the measurement conditions, and the method for determining the composition ratio are described in detail.

(Analysis and Measurement of the Composition of an Ester Using GPC Columns)

As the GPC columns, four columns of styrene divinylbenzene-based TSK-GEL G4000HHR, 5 μm, 7.8×300 mm, TSK-GEL G3000HHR, 5 μm, 7.8×300 mm, TSK-GEL G2000HHR, 5 μm, 7.8×300 mm, and TSK-GEL G3000HHR, 5 μm, 7.8×300 mm (all manufactured by TOSOH CORPORATION) were used sequentially connected in series, and as a mobile phase, tetrahydrofuran was used, in order to separate raw materials "S (% by area)", a monoester "A (% by area)", a diester "B (% by area)", a triester "C (% by area)", and a tetra- or higher valent polyester "X (% by area)", which were present in each of the ester compositions. Using the measurement results, the composition ratio of each component was determined.

HPLC was performed by using a differential refraction index detector as a detector (Shimadzu pump unit for high-performance liquid chromatography, LC-10AD, Shimadzu column oven for high-performance chromatography, CTO-10A, and Shimadzu differential refraction index detector for high-performance chromatography RID-6A, all manufactured by SHIMADZU CORPORATION).

Further, measurements were carried out under the condition of a column temperature of HPLC of 40° C., and a flow rate of the mobile phase of 0.5 mL/min.

(Analysis of the Composition of an Ester Using ODS Columns)

As the ODS columns, Kaseisorb LC ODS2000, 5 µm, 4.6×150 mm (manufactured by Tokyo Chemical Industry Co., Ltd.) was used, and as a mobile phase, a mixed solution of tetrahydrofuran:methanol=55:45 (volume ratio) was used, in order to separate a tetraester "d (% by area)", a pentaester "e (% by area)", a hexaester "f (% by area)", a heptaester "g (% by area)", and an octaester "h (% by area)", which were present in each of the ester compositions. Using the measurement results, the composition ratio of each component in the polyester was determined.

HPLC was performed by using a differential refraction index detector as a detector (Shimadzu pump unit for high-performance liquid chromatography, LC-10AD, Shimadzu column oven for high-performance chromatography, CTO-10A, and Shimadzu differential refraction index detector for high-performance chromatography RID-6A, all manufactured by SHIMADZU CORPORATION).

Further, measurements were carried out under the condition of a column temperature of HPLC of 40° C., and a flow rate of the mobile phase of 0.8 mL/min.

Further, since in the analysis using the ODS columns, the peaks derived from raw materials, a monoester, a diester, and a triester overlap the noise peaks derived from the solvent, it is impossible to attain precise separation. Thus, in the analysis and measurement of the composition of the ester using ODS column, only the composition ratios of a tetraester, a pentaester, a hexaester, a heptaester, and an octaester were taken for measurements.

(Methods for Determining the Composition Ratio of Each Component in the Trehalose Fatty Acid Ester Compositions and the Comparative Sugar Fatty Acid Ester Compositions)

The composition ratio of raw materials "S (% by area)", the composition ratio of a monoester "A (% by area)", the composition ratio of a diester "B (% by area)", and the composition ratio of a triester "C (% by area)" in the trehalose fatty acid ester composition and the comparative sugar fatty acid ester composition were determined using the measurement results, as described in the analysis of the composition of an ester using GPC columns, as described above.

Furthermore, the composition ratio of a tetraester "D (% by area)", the composition ratio of a pentaester "E (% by area)", the composition ratio of a hexaester "F (% by area)", the composition ratio of a heptaester "G (% by area)", and the composition ratio of an octaester "H (% by area)" were determined from the composition ratio of a polyester "X (% by area)" as measured in the GPC columns, and the composition ratio of a tetraester "d (% by area)", the composition ratio of a pentaester "e (% by area)", the composition ratio of a hexaester "f (% by area)", the composition ratio of a heptaester "g (% by area)", and the composition ratio of an octaester "h (% by area)" as described in the analysis of the composition of an ester using ODS columns, as described above, by using the following equation. Based on this, the composition ratio of each component (a tetraester, a pentaester, a hexaester, a heptaester, and an octaester) was determined.

Equation:

If the sum of the areas (%) of a polyester (a tetraester, a pentaester, a hexaester, a heptaester, and an octaester), as measured in the ODS columns, was taken as "Y (% by area)", the result will be as follows:

$$Y(\% \text{ by area}) = d + e + f + g + h.$$

From the composition ratio "X (% by area)" of a polyester, as measured in the GPC columns, and the composition ratio "d (% by area)" of a tetraester, as measured in the ODS columns, for example, the composition ratio of a tetraester was determined as follows:

$$D(\% \text{ by area}) = X \times d / Y.$$

The composition ratios of the following a pentaester "E (% by area)", a hexaester "F (% by area)", a heptaester "G (% by area)", and an octaester "H (% by area)" were determined by using the same methods as described above.

Example 1

Trehalose Fatty Acid Ester Composition 1 Obtained by Transesterifying Trehalose with Methyl Isostearate.

162.5 g (0.43 mole) of trehalose-dihydrate (manufactured by Hayashibara Group., TREHA-HT), 1100.3 g (3.66 moles) of methyl isostearate (prepared by a routine method, acid value: 2.0), 3.3 g of potassium carbonate (manufactured by Wako Pure Chemical Industries, Ltd., potassium carbonate), and 63.1 g of sodium stearate (manufactured by Wako Pure Chemical Industries, Ltd., sodium stearate) were charged into a 2000-ml four-neck flask equipped with a stirrer, a thermometer, a cork-stoppered nitrogen gas inlet tube, and a cork-stoppered glass tube, and stirred at 95° C., while drying moisture off under reduced pressure. Nitrogen gas was used to return the inner pressure of the four-neck flask to normal pressure, and as a catalyst, 8.1 g of potassium carbonate (manufactured by Wako Pure Chemical Industries, Ltd., potassium carbonate) was added thereto, and the pressure was reduced again. The mixture was reacted at 110 to 170° C. for 48 hours under pressure. After completion of the reaction, the mixture was diluted with 1000 ml of xylene, and filtered, and the filtrate was slowly and repeatedly washed with warm water until the aqueous solution layer that was a lower layer was substantially neutralized. After completion of the washing, the xylene layer that was an upper layer was dried under pressure, and xylene was distilled off. Further, the mixture was decolored with activated carbon and activated clay, and then deodorized under distillation treatment by an ordinary method, to obtain 815 g of a desired trehalose fatty acid ester composition 1 having a hydroxyl value of 28 and a saponification value of 176.

The analysis results of the composition of this trehalose fatty acid ester composition 1 by means of HPLC are shown in Table 1.

Example 2

Trehalose Fatty Acid Ester Composition 2 Obtained by Transesterifying Trehalose with Methyl Isostearate.

170.1 g (0.45 mole) of trehalose•dihydrate (manufactured by Hayashibara Group., TREHA-HT), 988.9 g (3.29 moles) of methyl isostearate (prepared by a routine method, acid value: 2.0), 69.5 g of isostearic acid (manufactured by Cognis Corporation, Emersol, 874), and 113.2 g of a 10 wt % aqueous solution of sodium hydroxide were charged into a 2000-ml four-neck flask equipped with a stirrer, a thermometer, a cork-stoppered nitrogen gas inlet tube, and a cork-stoppered glass tube, and stirred at 95° C., while drying moisture off under reduced pressure. Nitrogen gas was used to return the inner pressure of the four-neck flask to normal pressure, and as a catalyst, 8.5 g of potassium carbonate (manufactured by Wako Pure Chemical Industries, Ltd., potassium carbonate)

was added thereto, and the pressure was reduced again. The mixture was reacted at 110 to 170° C. for 48 hours under pressure. After completion of the reaction, the mixture was diluted with 1000 ml of xylene, and filtered, and the filtrate was slowly and repeatedly washed with warm water until the aqueous solution layer that was a lower layer was substantially neutralized. After completion of the washing, the xylene layer that was an upper layer was dried under pressure, and xylene was distilled off. Further, the mixture was decolored with activated carbon and activated clay, and then deodorized under distillation treatment by an ordinary method, to obtain 695 g of a desired trehalose fatty acid ester composition 2 having a hydroxyl value of 42 and a saponification value of 172.

The analysis results of the composition of this trehalose fatty acid ester composition 2 by means of HPLC are shown in Table 1.

Example 3

Trehalose Fatty Acid Ester Composition 3 Obtained by Transesterifying Trehalose with Methyl Isostearate.

207.9 g (0.55 mole) of trehalose•dihydrate (manufactured by Hayashibara Group., TREHA-HT), 1126.6 g (3.74 moles) of methyl isostearate (prepared by a routine method, acid value: 2.0), 74.1 g of isostearic acid (manufactured by Cognis Corporation, Emersol, 874), and 120.2 g of a 10 wt % aqueous solution of sodium hydroxide were charged into a 2000-ml four-neck flask equipped with a stirrer, a thermometer, a cork-stoppered nitrogen gas inlet tube, and a cork-stoppered glass tube, and stirred at 95° C., while drying moisture off under reduced pressure. Nitrogen gas was used to return the inner pressure of the four-neck flask to normal pressure, and as a catalyst, 10.4 g of potassium carbonate (manufactured by Wako Pure Chemical Industries, Ltd., potassium carbonate) was added thereto, and the pressure was reduced again. The mixture was reacted at 110 to 170° C. for 48 hours under pressure. After completion of the reaction, the mixture was diluted with 1500 ml of xylene, and filtered, and the filtrate was slowly and repeatedly washed with warm water until the aqueous solution layer that was a lower layer was substantially neutralized. After completion of the washing, the xylene layer that was an upper layer was dried under pressure, and xylene was distilled off. Further, the mixture was decolored with activated carbon and activated clay, and then deodorized under distillation treatment by an ordinary method, to obtain 805 g of a desired trehalose fatty acid ester composition 3 having a hydroxyl value of 57 and a saponification value of 168.

The analysis results of the composition of this trehalose fatty acid ester composition 3 by means of HPLC are shown in Table 1.

Example 4

Trehalose Fatty Acid Ester Composition 4 Obtained by Transesterifying Trehalose with Methyl Isostearate.

241.9 g (0.64 mole) of trehalose•dihydrate (manufactured by Hayashibara Group., TREHA-HT), 1001.9 g (3.33 moles) of methyl isostearate (prepared by a routine method, acid value: 2.0), 3.0 g of potassium carbonate (manufactured by Wako Pure Chemical Industries, Ltd., potassium carbonate), and 62.2 g of sodium stearate (manufactured by Wako Pure Chemical Industries, Ltd., sodium stearate) were charged into a 2000-ml four-neck flask equipped with a stirrer, a thermometer, a cork-stoppered nitrogen gas inlet tube, and a cork-stoppered glass tube, and stirred at 95° C., while drying moisture off under reduced pressure. Nitrogen gas was used to return the inner pressure of the four-neck flask to normal pressure, and as a catalyst, 12.1 g of potassium carbonate (manufactured by Wako Pure Chemical Industries, Ltd., potassium carbonate) was added thereto, and the pressure was reduced again. The mixture was reacted at 110 to 170° C. for 48 hours under pressure. After completion of the reaction, the mixture was diluted with 1000 ml of xylene and 500 ml of butyl acetate, and filtered, and the filtrate was slowly and repeatedly washed with warm water until the aqueous solution layer that was a lower layer was substantially neutralized. After completion of the washing, the xylene layer that was an upper layer was dried under pressure, and xylene was distilled off. Further, the mixture was decolored with activated carbon and activated clay, and then deodorized under distillation treatment by an ordinary method, to obtain 705 g of a desired trehalose fatty acid ester composition 4 having a hydroxyl value of 94 and a saponification value of 166.

The analysis results of the composition of this trehalose fatty acid ester composition 4 by means of HPLC are shown in Table 1.

Example 5

Trehalose Fatty Acid Ester Composition 5 Obtained by Transesterifying Trehalose with Methyl Isostearate.

283.5 g (0.75 mole) of trehalose•dihydrate (manufactured by Hayashibara Group., TREHA-HT), 880.6 g (2.93 moles) of methyl isostearate (prepared by a routine method, acid value: 2.0), 69.8 g of isostearic acid (manufactured by Cognis Corporation, Emersol, 874), and 112.0 g of a 10 wt % aqueous solution of sodium hydroxide were charged into a 2000-ml four-neck flask equipped with a stirrer, a thermometer, a cork-stoppered nitrogen gas inlet tube, and a cork-stoppered glass tube, and stirred at 95° C., while drying moisture off under reduced pressure. Nitrogen gas was used to return the inner pressure of the four-neck flask to normal pressure, and as a catalyst, 12.1 g of potassium carbonate (manufactured by Wako Pure Chemical Industries, Ltd., potassium carbonate) was added thereto, and the pressure was reduced again. The mixture was reacted at 110 to 170° C. for 48 hours under pressure. After completion of the reaction, the mixture was diluted with 750 ml of xylene and 750 ml of butyl acetate, and filtered, and the filtrate was slowly and repeatedly washed with warm water until the aqueous solution layer that was a lower layer was substantially neutralized. After completion of the washing, the layer of a mixture of xylene and butyl acetate that was an upper layer was dried under pressure, and butyl acetate and xylene were distilled off. Further, the mixture was decolored with activated carbon and activated clay, and then deodorized under distillation treatment by an ordinary method, to obtain 673 g of a desired trehalose fatty acid ester composition 5 having a hydroxyl value of 142 and a saponification value of 159.

The analysis results of the composition of this trehalose fatty acid ester composition 5 by means of HPLC are shown in Table 1.

Example 6

Trehalose Fatty Acid Ester Composition 6 Obtained by Transesterifying Trehalose with Methyl Isostearate.

37.8 g (0.1 mole) of trehalose•dihydrate (manufactured by Hayashibara Group., TREHA-HT), 90.3 g (0.3 mole) of methyl isostearate (prepared by a routine method, acid value: 2), and 330 ml of dimethyl sulfoxide (manufactured by Wako Pure Chemical Industries, Ltd., dimethyl sulfoxide) were charged into a 500-ml four-neck flask equipped with a stirrer, a thermometer, a cork-stoppered nitrogen gas inlet tube, and a cork-stoppered glass tube, and stirred at 70° C. under supply of nitrogen gas, to dissolve trehalose. The mixture was dried under reduced pressure under stirring at 75 to 80° C. for 1 hour. Nitrogen gas was used to return the inner pressure of the four-neck flask to normal pressure, and as a catalyst, 1.9 g of potassium carbonate (manufactured by Wako Pure Chemical Industries, Ltd., potassium carbonate) was added thereto, and the pressure was reduced again. The mixture was reacted at 80 to 95° C. for 12 hours under pressure. After completion of the reaction, the mixture was neutralized with citric acid monohydrate (manufactured by Wako Pure Chemical Industries, Ltd., citric acid monohydrate), and dimethyl sulfoxide was distilled off under pressure. The resulting mixture was further diluted with 200 ml of ethyl acetate (manufactured by Wako Pure Chemical Industries, Ltd., ethyl acetate), and 100 ml of 2-propanol (manufactured by Wako Pure Chemical Industries, Ltd., 2-propanol), and decolored with activated carbon and activated clay. The activated carbon and the activated clay were separated by filtration, and ethyl acetate and 2-propanol were distilled off from the mixture solution under reduced pressure to obtain 103 g of a desired trehalose fatty acid ester composition 6 having a hydroxyl value 238 and a saponification value of 146.

The analysis results of the composition of this trehalose fatty acid ester composition 6 by means of HPLC are shown in Table 1.

Example 7

Trehalose Fatty Acid Ester Composition 7 Obtained by Transesterifying Trehalose with Methyl Isostearate.

151.2 g (0.4 mole) of trehalose•dihydrate (manufactured by Hayashibara Group., TREHA-HT), 206.8 g (0.68 mole) of methyl isostearate (prepared by a routine method, acid value: 4), and 500 ml of dimethyl sulfoxide (manufactured by Wako Pure Chemical Industries, Ltd., dimethyl sulfoxide) were charged into a 1000-ml four-neck flask equipped with a stirrer, a thermometer, a cork-stoppered nitrogen gas inlet tube, and a cork-stoppered glass tube, and stirred at 70° C. under supply of nitrogen gas, to dissolve trehalose. The mixture was dried under reduced pressure under stirring at 75 to 80° C. for 1 hour. Nitrogen gas was used to return the inner pressure of the four-neck flask to normal pressure, and as a catalyst, 7.6 g of potassium carbonate (manufactured by Wako Pure Chemical Industries, Ltd., potassium carbonate) was added thereto, and the pressure was reduced again. The mixture was reacted at 80 to 95° C. for 12 hours under pressure. After completion of the reaction, the mixture was neutralized with citric acid monohydrate (manufactured by Wako Pure Chemical Industries, Ltd., citric acid monohydrate), and dimethyl sulfoxide was distilled off under pressure. The resulting mixture was further diluted with 400 ml of ethyl acetate (manufactured by Wako Pure Chemical Industries, Ltd., ethyl acetate), and 200 ml of 2-propanol (manufactured by Wako Pure Chemical Industries, Ltd., 2-propanol), and decolored with activated carbon and activated clay. The activated carbon and the activated clay were separated by filtration, and ethyl acetate and 2-propanol were distilled off from the mixture solution under reduced pressure to obtain 225 g of a desired trehalose fatty acid ester composition 7 having a hydroxyl value 350 and a saponification value of 122.

The analysis results of the composition of this trehalose fatty acid ester composition 7 by means of HPLC are shown in Table 1.

Example 8

Paste Trehalose Fatty Acid Ester Composition 8 Obtained by Transesterifying Trehalose with Methyl Stearate and Methyl Isostearate 207.9 g (0.55 mole) of trehalose•dihydrate (manufactured by Hayashibara Group., TREHA-HT), 493.1 g (1.65 moles) of methyl stearate (prepared by a routine method, acid value: 0.6), 496.7 g (1.67 moles) of methyl isostearate (prepared by a routine method, acid value: 2.0), 71.9 g of isostearic acid (manufactured by Cognis Corporation, Emersol, 874), and 111.3 g of a 10 wt % aqueous solution of sodium hydroxide were charged into a 2000-ml four-neck flask equipped with a stirrer, a thermometer, a cork-stoppered nitrogen gas inlet tube, and a cork-stoppered glass tube, and stirred at 95° C., while drying moisture off under reduced pressure. Nitrogen gas was used to return the inner pressure of the four-neck flask to normal pressure, and as a catalyst, 10.4 g of potassium carbonate (manufactured by Wako Pure Chemical Industries, Ltd., potassium carbonate) was added thereto, and the pressure was reduced again. The mixture was reacted at 110 to 170° C. for 48 hours under pressure. After completion of the reaction, the mixture was diluted with 1500 ml of xylene, and filtered, and the filtrate was slowly and repeatedly washed with warm water until the aqueous solution layer that was a lower layer was substantially neutralized. After completion of the washing, the xylene layer that was an upper layer was dried under pressure, and xylene was distilled off. Further, the mixture was decolored with activated carbon and activated clay, and then deodorized under distillation treatment by an ordinary method, to obtain 733 g of a desired paste trehalose fatty acid ester composition 8 having a hydroxyl value of 53 and a saponification value of 174.

The analysis results of the composition of this trehalose fatty acid ester composition 8 by means of HPLC are shown in Table 1.

Example 9

Paste Trehalose Fatty Acid Ester Composition 9 Obtained by Transesterifying Trehalose with Methyl Stearate and Methyl Isostearate 241.9 g (0.64 mole) of trehalose•dihydrate (manufactured by Hayashibara Group., TREHA-HT), 655.1 g (2.20 moles) of methyl isostearate (prepared by a routine method, acid value: 2.0), 325.0 g (1.09 moles) of methyl stearate (prepared by a routine method, acid value: 0.5), 73.3 g of isostearic acid (manufactured by Cognis Corporation, Emersol, 874), and 114.8 g of a 10 wt % aqueous solution of sodium hydroxide were charged into a 2000-ml four-neck flask equipped with a stirrer, a thermometer, a cork-stoppered nitrogen gas inlet tube, and a cork-stoppered glass tube, and stirred at 95° C., while drying moisture off under reduced pressure. Nitrogen gas was used to return the inner pressure of the four-neck flask to normal pressure, and as a catalyst, 12.1 g of potassium carbonate (manufactured by Wako Pure Chemical Industries, Ltd., potassium carbonate) was added thereto, and the pressure was reduced again. The mixture was reacted at 110 to 170° C. for 48 hours under pressure. After completion of the reaction, the mixture was diluted with 1500 ml of xylene, and filtered, and the filtrate was slowly and repeatedly washed with warm water until the aqueous solution layer that was a lower layer was substantially neutralized. After completion of the washing, the xylene layer that was an upper layer was dried under pressure, and xylene was distilled off. Further, the mixture was decolored with activated carbon and activated clay, and then deodorized under distillation treatment by an ordinary method, to obtain 750 g of a desired paste trehalose fatty acid ester composition 9 having a hydroxyl value of 93 and a saponification value of 167.

The analysis results of the composition of this trehalose fatty acid ester composition 9 by means of HPLC are shown in Table 1.

Comparative Example 1

Comparative Sugar Fatty Acid Ester Composition 1 Obtained by Transesterifying the Trehalose Fatty Acid Ester Composition with Methyl Isostearate 300 g of the trehalose fatty acid ester composition 4 (the compound prepared in EXAMPLE 4, hydroxyl value: 94) and 299.5 g (twice the required amount as determined from the hydroxyl value of the trehalose fatty acid ester composition 4) of methyl isostearate (prepared by a routine method, acid value: 4.0) were charged into a 1000-ml four-neck flask equipped with a stirrer, a thermometer, a cork-stoppered nitrogen gas inlet tube, and a cork-stoppered glass tube, and stirred at 95° C., while drying under reduced pressure. Nitrogen gas was used to return the inner pressure of the four-neck flask to normal pressure, and as a catalyst, 6.6 g of potassium carbonate (manufactured by Wako Pure Chemical Industries, Ltd., potassium carbonate) was added thereto, and the pressure was reduced again. The mixture was reacted at 110 to 170° C. for 48 hours under pressure. After completion of the reaction, the mixture was diluted with 1000 ml of xylene, and filtered, and the filtrate was slowly and repeatedly washed with warn water until the aqueous solution layer that was a lower layer was substantially neutralized. After completion of the washing, the xylene layer that was an upper layer was dried under pressure, and xylene was distilled off. Further, the mixture was decolored with activated carbon and activated clay, and then deodorized under distillation treatment by an ordinary method, to obtain 430 g of a desired comparative sugar fatty acid ester composition I having a hydroxyl value of 5 and a saponification value of 168.

The analysis results of the composition of this comparative sugar fatty acid ester composition 1 by means of HPLC are shown in Table 1.

Comparative Example 2

Comparative Sugar Fatty Acid Ester Composition 2 Obtained by Esterifying Sucrose with Methyl Isostearate 68.4 g (0.2 mole) of sucrose (manufactured by Wako Pure Chemical Industries, Ltd., sucrose), 572.5 g (1.80 moles) of methyl isostearate (prepared by a routine method, acid value: 12.5), 5.1 g of sodium hydroxide (manufactured by Wako Pure Chemical Industries, Ltd., potassium carbonate), and 100 g of water were charged into a 1000-ml four-neck flask equipped with a stirrer, a thermometer, a cork-stoppered nitrogen gas inlet tube, and a cork-stoppered glass tube, and stirred at 95° C., while drying under reduced pressure. Nitrogen gas was used to return the inner pressure of the four-neck flask to normal pressure, and as a catalyst, 0.34 g of potassium carbonate (manufactured by Wako Pure Chemical Industries, Ltd., potassium carbonate) was added thereto, and the pressure was reduced again. The mixture was reacted at 100 to 170° C. for 48 hours under pressure. After completion of the reaction, the mixture was diluted with 500 ml of xylene, and filtered, and the filtrate was slowly and repeatedly washed with warm water until the aqueous solution layer that was a lower layer was substantially neutralized. After completion of the washing, the xylene layer that was an upper layer was dried under pressure, and xylene was distilled off. Further, the mixture was decolored with activated carbon and activated clay, and then deodorized under distillation treatment by an ordinary method, to obtain 302 g of a desired comparative sugar fatty acid ester composition 2 having a hydroxyl value of 28 and a saponification value of 180.

The analysis results of the composition of this comparative sugar fatty acid ester composition 2 by means of HPLC are shown in Table 1.

Comparative Example 3

Comparative Sugar Fatty Acid Ester Composition 3 Obtained by Transesterifying Sucrose with Methyl Isostearate 88.9 g (0.26 mole) of sucrose (manufactured by Dai-Nippon Meiji Sugar Co., Ltd., Granulated sugar), 492.6 g (1.56 moles) of methyl isostearate (prepared by a routine method, acid value: 11.1), and 8.5 g of potassium carbonate (manufactured by Wako Pure Chemical Industries, Ltd., potassium carbonate) were charged into a 1000-ml four-neck flask equipped with a stirrer, a thermometer, a cork-stoppered nitrogen gas inlet tube, and a cork-stoppered glass tube, and stirred at 95° C., while drying moisture off under reduced pressure. Nitrogen gas was used to return the inner pressure of the four-neck flask to normal pressure, and as a catalyst, 3.6 g of potassium carbonate (manufactured by Wako Pure Chemical Industries, Ltd., potassium carbonate) was added thereto, and the pressure was reduced again. The mixture was reacted at 110 to 170° C. for 48 hours under pressure. After completion of the reaction, the mixture was diluted with 1000 ml of xylene, and filtered, and the filtrate was slowly and repeatedly washed with warm water until the aqueous solution layer that was a lower layer was substantially neutralized. After completion of the washing, the xylene layer that was an upper layer was dried under pressure, and xylene was distilled off. Further, the mixture was decolored with activated carbon and activated clay, and then deodorized under distillation treatment by an ordinary method, to obtain 287 g of a desired comparative sugar fatty acid ester composition 3 having a hydroxyl value of 53 and a saponification value of 179.

The analysis results of the composition of this comparative sugar fatty acid ester composition 3 by means of HPLC are shown in Table 1.

Comparative Example 4

Comparative Sugar Fatty Acid Ester Composition 4 Obtained by Transesterifying Sucrose with Methyl Isostearate 51.3 g (0.15 mole) of sucrose (manufactured by Dai-Nippon Meiji Sugar Co., Ltd., Granulated sugar), 152.1 g (0.51 mole) of methyl isostearate (prepared by a routine method, acid value: 0.2), and 400 ml of dimethyl sulfoxide (manufactured by Wako Pure Chemical Industries, Ltd., dimethyl sulfoxide) were charged into a 1000-ml four-neck flask equipped with a stirrer, a thermometer, a cork-stoppered nitrogen gas inlet tube, and a cork-stoppered glass tube, and stirred at 80° C. under supply of nitrogen gas, to dissolve sucrose. The mixture was dried under reduced pressure under stirring for 1 hour. Nitrogen gas was used to return the inner pressure of the four-neck flask to normal pressure, and as a catalyst, 2.6 g of potassium carbonate (manufactured by Wako Pure Chemical Industries, Ltd., potassium carbonate) was added thereto, and the pressure was reduced again. The mixture was reacted at 90 to 95° C. for 12 hours under pressure. After completion of the reaction, the mixture was neutralized with citric acid monohydrate (manufactured by Wako Pure Chemical Industries, Ltd., citric acid monohydrate), and dimethyl sulfoxide was distilled off under pressure. The resulting mixture was further diluted with 400 ml of ethyl acetate (manufactured by Wako Pure Chemical Industries, Ltd., ethyl acetate), and 200 ml of 2-propanol (manufactured by Wako Pure Chemical Industries, Ltd., 2-propanol), and decolored with activated carbon and activated clay. The activated carbon and the activated clay were separated by filtration, and ethyl acetate and 2-propanol were distilled off from the mixture solution under reduced pressure to obtain 145 g of a desired liquid comparative sugar fatty acid ester composition 4 having a hydroxyl value 185 and a saponification value of 147.

The analysis results of the composition of this comparative sugar fatty acid ester composition 4 by means of HPLC are shown in Table 1.

Comparative Example 5

Comparative Sugar Fatty Acid Ester Composition 5 Obtained by Transesterifying Sucrose with Methyl Isostearate 136.8 g (0.4 mole) of sucrose (manufactured by Dai-Nippon Meiji Sugar Co., Ltd., Granulated sugar), 206.8 g (0.68 mole) of methyl isostearate (prepared by a routine method, acid value: 4.0), and 500 ml of dimethyl sulfoxide (manufactured by Wako Pure Chemical Industries, Ltd., dimethyl sulfoxide) were charged into a 1000-ml four-neck flask equipped with a stirrer, a thermometer, a cork-stoppered nitrogen gas inlet tube, and a cork-stoppered glass tube, and stirred at 80° C. under supply of nitrogen gas, to dissolve sucrose. The mixture was dried under reduced pressure under stirring for 1 hour. Nitrogen gas was used to return the inner pressure of the four-neck flask to normal pressure, and as a catalyst, 6.8 g of potassium carbonate (manufactured by Wako Pure Chemical Industries, Ltd., potassium carbonate) was added thereto, and the pressure was reduced again. The mixture was reacted at 90 to 95° C. for 12 hours under pressure. After completion of the reaction, the mixture was neutralized with citric acid monohydrate (manufactured by Wako Pure Chemical Industries, Ltd., citric acid monohydrate), and dimethyl sulfoxide was distilled off under pressure. The resulting mixture was further diluted with 400 ml of ethyl acetate (manufactured by Wako Pure Chemical Industries, Ltd., ethyl acetate), and 200 ml of 2-propanol (manufactured by Wako Pure Chemical Industries, Ltd., 2-propanol), and decolored with activated carbon and activated clay. The activated carbon and the activated clay were separated by filtration, and ethyl acetate and 2-propanol were distilled off from the mixture solution under reduced pressure to obtain 232 g of a desired comparative sugar fatty acid ester composition 5 having a hydroxyl value 343 and a saponification value of 138.

The analysis results of the composition of the comparative sugar fatty acid ester composition 5 by means of HPLC are shown in Table 1.

(Purification of Each Ester in the Trehalose Fatty Acid Ester Composition)

Trehalose Octaisostearic Acid Ester Through Trehalose Monoisostearic Acid Ester

The ester compositions of COMPARATIVE EXAMPLE 1, EXAMPLE 4, EXAMPLE 6, and EXAMPLE 7 were repeatedly subject to column purification using a mixed solvent of hexane/ethyl acetate/methanol (stepwise elution was performed by increasing the concentration of ethyl acetate in a range of the mixing volume ratios of hexane/ethyl acetate in a range of 15/1 to 0/1, and then stepwise elution was further performed by increasing the concentration of methanol in a range of the ratio of ethyl acetate/methanol in a range of 1/0 to 1/2) by means of available silica gel for column chromatography (manufactured by Wako Pure Chemical Industries, Ltd. WACOSIL C-200), to obtain each ester composition having a purity of 75% by area or more. Each of the resulting esters has a hydroxyl value as follows: trehalose octaisostearic acid ester: 4, trehaloseheptaisostearic acid ester: 32, trehalosehexaisostearic acid ester: 63, trehalosepentaisostearic acid ester: 101, trehalose tetraisostearic acid ester: 156, trehalosetriisostearic acid ester: 234, trehalosediisostearic acid ester: 390, and trehalosemonoisostearic acid ester: 635.

The analysis results of the composition of each of these esters by means of HPLC are shown in Table 2.

For each of the trehalose fatty acid ester compositions and the comparative sugar fatty acid ester compositions obtained in EXAMPLES 1 to 9, and COMPARATIVE EXAMPLES 1 to 5, the composition analysis was performed using the measurement method and the determination method, as described above. For raw materials=S, a monoester (1)=A, a diester (2)=B, a triester (3)=C, a tetraester (4)=D, a pentaester (5)=E, a hexaester (6)=F, a heptaester (7)=G, and an octaester (8)=H in each of the fatty acid ester compositions, the composition ratio (% by area) are shown in Table 1.

Furthermore, the analysis results of a monoester through an octaester obtained by column purification are shown in Table 2

Analysis Results of the Composition of the Trehalose Fatty Acid Ester Compositions, and the Comparative Sugar Fatty Acid Ester Composition 1

Table 1 shows that the trehalose fatty acid ester compositions 1 to 9 of the present invention have a mixture of esters having a low content of a monoester having low oil and high crystallinity as low as 30% by area or less, and having a hydroxyl group of the trehalose highly substituted with fatty acid esters, and that the compositions exhibit oil solubility.

It is also shown that the ratio of an octaester in which all of the hydroxyl groups of the trehalose are substituted with fatty acid esters is 45% by area or less, and a half or more of the composition was composed of a diester through a heptaester having excellent dispersion ability.

TABLE 1

| Name of sample | Raw materials | % by area of each ester as determined by HPLC analysis | | | | | | | |
|---|---|---|---|---|---|---|---|---|---|
| | | 1 | 2 | 3 | 4 | 5 | 6 | 7 | 8 |
| Trehalose fatty acid ester composition 1 | 0.4 | 0 | 0 | 0 | 2.5 | 8.0 | 16.3 | 32.0 | 40.8 |
| Trehalose fatty acid ester composition 2 | 0 | 0 | 0 | 0.7 | 3.8 | 13.1 | 23.3 | 33.0 | 26.1 |
| Trehalose fatty acid ester composition 3 | 0 | 0 | 0 | 3.5 | 8.9 | 20.8 | 26.2 | 26.6 | 14.0 |
| Trehalose fatty acid ester composition 4 | 0 | 0 | 1.2 | 7.5 | 18.6 | 25.3 | 23.9 | 16.1 | 7.4 |
| Trehalose fatty acid ester composition 5 | 0.5 | 0.3 | 6.0 | 17.1 | 27.5 | 25.7 | 15.0 | 6.5 | 1.4 |
| Trehalose fatty acid ester composition 6 | 4.8 | 5.0 | 21.4 | 29.3 | 22.5 | 12.0 | 3.8 | 0.9 | 0.3 |
| Trehalose fatty acid ester composition 7 | 0 | 20.7 | 34.1 | 26.8 | 12.4 | 5.1 | 0.9 | 0 | 0 |
| Trehalose fatty acid ester composition 8 | 0.7 | 0 | 0 | 1.7 | 8.4 | 18.0 | 24.8 | 27.8 | 18.6 |
| Trehalose fatty acid ester composition 9 | 0.6 | 0 | 2.4 | 8.0 | 18.6 | 23.3 | 22.2 | 17.6 | 7.3 |
| Composition of EXAMPLE 11 | 1.2 | 1.3 | 5.4 | 7.8 | 8.5 | 12.8 | 18.4 | 24.9 | 19.7 |
| Comparative sugar fatty acid ester composition 1 | 0 | 0 | 0 | 0 | 0 | 1.0 | 2.9 | 17.4 | 78.7 |
| Comparative sugar fatty acid ester composition 2 | 0.4 | 0 | 0 | 0 | 0 | 5.3 | 20.3 | 41.3 | 32.7 |
| Comparative sugar fatty acid ester composition 3 | 2.7 | 0 | 0 | 0.4 | 8.3 | 17.6 | 23.0 | 30.0 | 18.0 |
| Comparative sugar fatty acid ester composition 4 | 3.9 | 1.1 | 10.0 | 22.4 | 29.4 | 19.7 | 10.6 | 2.9 | 0 |
| Comparative sugar fatty acid ester composition 5 | 0 | 20.7 | 34.1 | 26.8 | 12.4 | 5.1 | 0.9 | 0 | 0 |

TABLE 2

| Name of sample | Raw materials | % by area of each ester as determined by HPLC analysis | | | | | | | |
|---|---|---|---|---|---|---|---|---|---|
| | | 1 | 2 | 3 | 4 | 5 | 6 | 7 | 8 |
| Trehalose octaisostearic acid ester | 0 | 0 | 0 | 0 | 0 | 0 | 0 | 18.2 | 81.8 |
| Trehalose heptaisostearic acid ester | 0 | 0 | 0 | 0 | 0 | 3.5 | 15.5 | 76.8 | 4.2 |
| Trehalose hexaisostearic acid ester | 0 | 0 | 0 | 0 | 3.0 | 10.3 | 77.7 | 9.0 | 0 |
| Trehalose pentaisostearic acid ester | 2.0 | 0 | 0 | 0 | 4.9 | 90.3 | 2.8 | 0 | 0 |
| Trehalose tetraisostearic acid ester | 0 | 0 | 0 | 0 | 95.7 | 4.3 | 0 | 0 | 0 |
| Trehalose triisostearic acid ester | 0 | 0 | 0 | 88.0 | 11.3 | 0.7 | 0 | 0 | 0 |
| Trehalose diisostearic acid ester | 0 | 1.9 | 98.1 | 0 | 0 | 0 | 0 | 0 | 0 |
| Trehalose monoisostearic acid ester | 0 | 97.1 | 2.9 | 0 | 0 | 0 | 0 | 0 | 0 |

Evaluation of extender dispersibility and color pigment dispersibility was conducted on the trehalose fatty acid ester compositions obtained in EXAMPLES 1 to 9, and the comparative sugar fatty acid ester compositions obtained in COMPARATIVE EXAMPLES 1 to 5. In addition, evaluation of extender dispersibility was also conducted on a monoester through an octaester obtained by column purification as described above. Hereinbelow, the evaluation methods and the evaluation results are described.

Evaluation of Extender Dispersibility (Sample to be Evaluated)

Evaluation of extender dispersibility was conducted on the trehalose fatty acid ester compositions 1 to 9, the comparative sugar fatty acid ester compositions 1 to 5, a monoester through an octaester obtained by column purification, and diglyceryl triisostearate (trade name: COSMOL 43V, manufactured by the Nisshin OilliO Group, Ltd.), diisostearyl malate (trade name: COSMOL 222, manufactured by the Nisshin OilliO Group, Ltd.), sorbitan sesquiisostearate (trade name: COSMOL 182V, manufactured by the Nisshin OilliO Group, Ltd.), sorbitan sesquioleate (trade name: COSMOL 82, manufactured by the Nisshin OilliO Group, Ltd.), polyglyceryl-10 pentaisostearate (trade name: Decaglyn 5-IS, manufactured by Nikko Chemicals Co., Ltd.), and polyoxyethylene.methyl polysiloxanecopolymer (trade name: KF-6015, manufactured by Shin-Etsu Chemical Co., Ltd.), generally used as a pigment dispersant in the applications of cosmetic products.

0.5 g (1.0% by mass relative to the total mass) of the pigment dispersant, 18.25 g of octyl palmitate as a dispersion medium (trade name: SALACOS P-8, manufactured by the Nisshin OilliO Group, Ltd.), and 31.25 g of mica titanium as a dispersoid (trade name: FlamencoGreen, manufactured by Engelhard Corporation) were charged into a 100-ml stainless beaker, and mixed under stirring at 90° C. for 30 minutes with a homomixer fitted with a Disper mill at a revolution rate that had been increased to 1500 rpm, to obtain a sample for evaluation of extender dispersibility.

(Evaluation Method)

The states and flowability of the obtained sample for evaluation of extender dispersibility were observed with the naked eye. Here, the evaluation criteria and the evaluation results are shown in Tables 3 and 4, respectively.

TABLE 3

| Evaluation criteria for extender dispersibility | |
|---|---|
| The state and flowability of the mixture | Evaluation |
| Found to have low stickiness, sufficient lastingness, and excellent flowability | S |
| Found to have lastingness and sufficient flowability | A |
| Found to have high viscosity and flowability in spite of some paste feeling | B |
| Being in a paste form, but having insufficient lastingness and flowability | C |
| Being not uniform with the remaining powders, and having insufficient flowability | D |
| Having no flowability | E |

TABLE 4

Evaluation results of extender (mica titanium) dispersibility

| Name of sample to be evaluated | Hydroxyl value | Ingredient I[Note 1] | Ingredient II[Note 2] | Evaluation |
|---|---|---|---|---|
| Trehalose fatty acid ester composition 1 | 28 | 2.5 | 89.1 | B |
| Trehalose fatty acid ester composition 2 | 42 | 4.5 | 83.4 | B |
| Trehalose fatty acid ester composition 3 | 57 | 12.4 | 66.8 | A |
| Trehalose fatty acid ester composition 4 | 94 | 27.3 | 47.4 | A |
| Trehalose fatty acid ester composition 5 | 142 | 50.5 | 22.9 | A |
| Trehalose fatty acid ester composition 6 | 238 | 73.2 | 5 | S |
| Trehalose fatty acid ester composition 7 | 350 | 73.3 | 0.9 | S |
| Trehalose fatty acid ester composition 8 | 53 | 10.1 | 71.2 | A |
| Trehalose fatty acid ester composition 9 | 93 | 29 | 47.1 | A |
| Comparative sugar fatty acid ester composition 1 | 5 | 0 | 99 | C |
| Comparative sugar fatty acid ester composition 2 | 28 | 0 | 94.3 | D |
| Comparative sugar fatty acid ester composition 3 | 53 | 8.7 | 71 | C |
| Comparative sugar fatty acid ester composition 4 | 185 | 61.8 | 13.5 | C |
| Comparative sugar fatty acid ester composition 5 | 343 | 73.3 | 0.9 | B |
| Trehalose octaisostearic acid ester | 4 | | | D |
| Trehalose heptaisostearic acid ester | 32 | | | C |
| Trehalose hexaisostearic acid ester | 63 | | | B |
| Trehalose pentaisostearic acid ester | 101 | | | A |
| Trehalose tetraisostearic acid ester | 156 | | | S |
| Trehalose triisostearic acid ester | 234 | | | S |
| Trehalose diisostearic acid ester | 390 | | | S |
| Trehalose monoisostearic acid ester | 635 | | | D |
| Diglyceryl triisostearate | | | | E |
| Diisostearyl malate | | | | E |
| Sorbitan sesquiisostearate | | | | D |
| Sorbitan sesquioleate | | | | D |
| Polyglyceryl-10 pentaisostearate | | | | D |
| Polyoxyethylene/methyl polysiloxane copolymer | | | | D |

Note 1) Ingredient I is the total amount of a diester, a triester, and a tetraester (% by area) in the trehalose fatty acid esters.
Note 2) Ingredient II is the total amount of a hexaester, a heptaester, and an octaester (% by area) in the trehalose fatty acid esters.

(Evaluation Results)

As shown from the results in Table 4, the trehalose fatty acid ester compositions 1 to 9 of the present invention have excellent extender dispersibility, when added even in an amount of 1.0% by mass, relative to 62.5% by mass of mica titanium as a dispersoid, and 36.5% by mass octyl palmitate as a dispersion medium.

On the other hand, the comparative sugar fatty acid ester compositions 1 to 5, and the pigment dispersants generally used in the applications of cosmetic products had low flowability, and thus could not impart satisfactory dispersion ability.

Further, the evaluation results of the products obtained by column purification confirmed that a monoester and an octaester had low dispersibility, a diester through a pentaester had excellent dispersibility, and among these, a diester through a tetraester had most excellent dispersibility.

0.5 g of the pigment dispersant (trehalose fatty acid esters 2, 4, and 7, diglyceryl triisostearate, diisostearyl malate, sorbitan sesquiisostearate, sorbitan sesquioleate, 3 polyglyceryl-10 pentaisostearate, and polyoxyethylene/methyl polysiloxane copolymer) (1.0% by mass relative to the total mass), 20.5 g of octyl palmitate as a dispersion medium (trade name: SALACOS P-8, manufactured by the Nisshin Oillio Group, Ltd.), and 29 g of talc as a dispersoid (trade name: talc JA46R, manufactured by ASADA MILLING Co., Ltd.) were charged into a 100-ml stainless beaker, and mixed under stirring at 90° C. for 30 minutes with a homomixer fitted with a Disper mill at a revolution rate that had been increased to 1500 rpm, to obtain a sample for evaluation of extender dispersibility.

(Evaluation Method)

The states and flowability of the obtained sample for evaluation of extender dispersibility were observed with the naked eye. Here, the evaluation criteria and the evaluation results are shown in Tables 5 and 6, respectively.

TABLE 5

Evaluation criteria for extender dispersibility

| State and flowability of the mixture | Evaluation |
|---|---|
| Found to have low stickiness, sufficient lastingness, and excellent flowability | S |
| Found to have lastingness and sufficient flowability | A |
| Found to have high viscosity and flowability in spite of some paste feeling | B |
| Being in a paste form, but having insufficient lastingness and flowability | C |
| Being not uniform with the remaining powders, and having insufficient flowability | D |
| Having no flowability | E |

TABLE 6

Evaluation results of extender (talc) dispersibility

| Name of sample to be evaluated | Hydroxyl value | Ingredient I Note 1) | Ingredient II Note 2) | Evaluation |
|---|---|---|---|---|
| Trehalose fatty acid ester composition 2 | 42 | 4.5 | 83.4 | B |

TABLE 6-continued

Evaluation results of extender (talc) dispersibility

| Name of sample to be evaluated | Hydroxyl value | Ingredient I Note 1) | Ingredient II Note 2) | Evaluation |
|---|---|---|---|---|
| Trehalose fatty acid ester composition 4 | 94 | 27.3 | 47.4 | A |
| Trehalose fatty acid ester composition 7 | 350 | 73.3 | 0.9 | S |
| Diglyceryl triisostearate | | | | E |
| Diisostearyl malate | | | | E |
| Sorbitan sesquiisostearate | | | | D |
| Sorbitan sesquioleate | | | | D |
| Polyglyceryl-10 pentaisostearate | | | | D |
| Polyoxyethylene•methyl polysiloxane | | | | D |

Note 1) Ingredient I is the total amount of a diester, a triester, and a tetraester (% by area) in the trehalose fatty acid esters.
Note 2) Ingredient II is the total amount of a hexaester, a heptaester, and an octaester (% by area) in the trehalose fatty acid esters.

(Evaluation Results)

As shown from the results in Table 6, the trehalose fatty acid ester compositions 2, 4, and 7 of the present invention had excellent extender dispersibility, when added even in an amount of 1.0% by mass, relative to 58% by mass of talc as a dispersoid, and 41% by mass octyl palmitate as a dispersion medium.

On the other hand, the pigment dispersants generally used in the applications of cosmetic products had low flowability, and thus could not impart satisfactory dispersion ability.

Evaluation of Color Pigment Dispersibility (Sample to be Evaluated)

Evaluation of color pigment dispersibility was conducted on the trehalose fatty acid ester compositions 1 to 7, the comparative sugar fatty acid ester compositions 1, 2, and 4, and diglyceryl triisostearate (trade name: COSMOL 43V, manufactured by the Nisshin OilliO Group, Ltd.), diisostearyl malate (trade name: COSMOL 222, manufactured by the Nisshin OilliO Group, Ltd.), and sorbitan sesquiisostearate (trade name: COSMOL 182V, manufactured by the Nisshin OilliO Group, Ltd.) used as a color pigment dispersant generally used in the applications of cosmetic products.

60 g of the sample to be evaluated, and 40 g of a color pigment (manufactured by Kishi Kasei Co., Ltd, Red No. 202 SG) were weighed into a 200-ml glass beaker, and premixed. Then, the mixture was kneaded using three rolls until it became uniform, to prepare a pigment adjuster.

25 g of the pigment adjuster prepared by the above-described method, and 75 g of liquid paraffin (trade name: HICOL K350, manufactured by KANEDA Co., Ltd.), or glyceryl tri-2-ethylhexanoate (trade name: T. I. O, manufactured by the Nisshin OilliO Group, Ltd.) as a dilution oil were weighed and charged into a 200-ml stainless jug, and mixed under stirring at room temperature for 5 minutes with a homomixer fitted with a Disper mill at 1000 rpm, to obtain a sample for evaluation of color pigment dispersibility.

(Evaluation Method)

The obtained sample for evaluation of color pigment dispersibility was put into a sample bottle with a lid, and the lid was closed. Then, the bottle was left to stand at room temperature for 2 months to evaluate color pigment dispersibility. For evaluation of color pigment dispersibility, the magnitude of the amount of the supernatant generated by settlement of the color pigment was observed with the naked eye, and evaluation was conducted based on the evaluation criteria as shown in Table 7. The evaluation results are shown in Table 8.

TABLE 7

Evaluation criteria for color pigment dispersibility

| Degree of settlement after standing to be left at room temperature for 2 months | Evaluation results |
|---|---|
| Settlement not found | A |
| Some supernatant found with a sign of settlement | B |
| Apparent supernatant found with settlement | C |

TABLE 8

Evaluation of color pigment dispersibility

| Name of sample to be evaluated | Hydroxyl value | Ingredient I[Note 1] | Ingredient II[Note 2] | Liquid paraffin | T. I. O. |
|---|---|---|---|---|---|
| Trehalose fatty acid ester composition 1 | 28 | 2.5 | 89.1 | B | B |
| Trehalose fatty acid ester composition 2 | 42 | 4.5 | 83.4 | A | A |
| Trehalose fatty acid ester composition 3 | 57 | 12.4 | 66.8 | A | A |
| Trehalose fatty acid ester composition 4 | 94 | 27.3 | 47.4 | A | A |
| Trehalose fatty acid ester composition 5 | 142 | 50.5 | 22.9 | A | A |

TABLE 8-continued

Evaluation of color pigment dispersibility

| | | | | Evaluation results | |
|---|---|---|---|---|---|
| Name of sample to be evaluated | Hydroxyl value | Ingredient I[Note 1)] | Ingredient II[Note 2)] | Liquid paraffin | T. I. O. |
| Trehalose fatty acid ester composition 6 | 238 | 73.2 | 5 | A | A |
| Trehalose fatty acid ester composition 7 | 350 | 73.3 | 0.9 | A | A |
| Comparative sugar fatty acid ester composition 1 | 5 | 0 | 99 | C | C |
| Comparative sugar fatty acid ester composition 2 | 28 | 0 | 94.3 | C | C |
| Comparative sugar fatty acid ester composition 4 | 185 | 61.8 | 13.5 | A | C |
| Diglyceryl triisostearate | | | | C | C |
| Diisostearyl malate | | | | C | C |
| Sorbitan sesquiisostearate | | | | A | C |

[Note 1)]Ingredient I is the total amount of a diester, a triester, and a tetraester (% by area) in the trehalose fatty acid esters.
[Note 2)]Ingredient II is the total amount of a hexaester, a heptaester, and an octaester (% by area) in the trehalose fatty acid esters.

(Evaluation Results)

As shown from the results in Table 8, the trehalose fatty acid ester compositions 1 to 7 of the present invention had no settlement of the color pigments, and satisfactory color pigment dispersibility, regardless of the kind of dilution oil. In particular, the trehalose fatty acid ester compositions 2 to 5 exhibited excellent dispersibility.

On the other hand, the comparative sugar fatty acid ester compositions 1, 2, and 4, and the color pigment dispersant generally used in the applications of cosmetic product was found to have settlement of the color pigment in either or both of dilution oils, and to have no satisfactory dispersibility.

Evaluation of dispersibility was also conducted on the other color pigments by the following method. 60 g of the samples to be evaluated (the trehalose fatty acid ester 4, diglyceryl triisostearate, diisostearyl malate, and sorbitan sesquiisostearate), and 40 g of Red No. 201 (DAITO KASEI KOGYO Co., Ltd., Red No. 201), Blue No. 1 Aluminum Lake (DAITO KASEI KOGYO Co., Ltd., Blue No. 1 Al Lake), Yellow No. 4 Aluminum Lake (Taketombo Co., Ltd., Yellow No. 4 Al Lake (A)), titanium oxide (Bayer AG, TRONOX R-KB-2), red iron oxide (Morishita Bengara Industrial Co. Ltd., Bengara Shippo, and Titan Kogyo K.K.), and yellow iron oxide (TAROX YELLOW LEMON), as the color pigments, were weighed into a 200-ml glass beaker, and premixed. Then, the mixture was kneaded using three rolls until it became uniform, to prepare a pigment adjuster.

25 g of the pigment adjuster prepared by the above-described method, and 75 g of liquid paraffin (trade name: HICOL K350, manufactured by KANEDA Co., Ltd.), or glyceryl tri-2-ethylhexanoate (trade name: T. I. O, manufactured by the Nisshin OilliO Group, Ltd.) as a dilution oil were weighed and charged into a 200-ml stainless jug, and mixed under stirring at room temperature for 5 minutes with a homomixer fitted with a Disper mill at 1000 rpm, to obtain a sample for evaluation of color pigment dispersibility.

(Evaluation Method)

1 ml of the obtained sample for evaluation of color pigment dispersibility was placed on a glass plate, and applied with a film applicator (JIS K5400) (trade name: DOCTOR BLADE, Type YD, 20 mm in width, 6 μm, Yoshimitsu Seiki) having a gap width of 6 μm, to give a thin film.

For evaluation of color pigment dispersibility, presence or absence of particle grains in the color pigment dispersion in the form of the thin film was observed with the naked eye, and evaluation was conducted based on the evaluation criteria in Table 9. The evaluation results are shown in Table 10.

TABLE 9

Evaluation criteria for color pigment dispersibility

| The state of the thin film after application with a 6 μm film applicator | Evaluation results |
|---|---|
| No aggregation of grains found | A |
| Slight aggregation of grains found | B |
| Clear aggregation of grains found | C |

TABLE 10

Evaluation results for color pigment dispersibility

| | | Evaluation results | |
|---|---|---|---|
| Kind of pigments | Name of the sample to be evaluated | Liquid paraffin | T. I. O. |
| Red No. 201 | Trehalose fatty acid ester composition 4 | A | A |
| | Diglyceryl triisostearate | C | C |
| | Diisostearyl malate | C | C |
| | Sorbitan sesquiisostearate | A | C |
| Blue No. 1 Aluminum Lake | Trehalose fatty acid ester composition 4 | A | A |
| | Diglyceryl triisostearate | C | C |
| | Diisostearyl malate | C | C |
| | Sorbitan sesquiisostearate | A | C |
| Yellow No. 4 Aluminum Lake | Trehalose fatty acid ester composition 4 | A | A |
| | Diglyceryl triisostearate | C | C |
| | Diisostearyl malate | C | C |
| | Sorbitan sesquiisostearate | A | C |
| Titanium oxide | Trehalose fatty acid ester composition 4 | A | A |
| | Diglyceryl triisostearate | C | C |
| | Diisostearyl malate | C | C |
| | Sorbitan sesquiisostearate | A | C |
| Red iron oxide | Trehalose fatty acid ester composition 4 | A | A |
| | Diglyceryl triisostearate | C | C |
| | Diisostearyl malate | C | C |
| | Sorbitan sesquiisostearate | A | C |
| Yellow iron oxide | Trehalose fatty acid ester composition 4 | A | A |
| | Diglyceryl triisostearate | C | C |
| | Diisostearyl malate | C | C |
| | Sorbitan sesquiisostearate | A | C |

Evaluation of Hardness Maintaining or Increasing Ability by Combining with Various Waxes (Sample to be Evaluated)

Evaluation of hardness was conducted on the trehalose fatty acid ester compositions 2, 3, 5, and 8, and the comparative sugar fatty acid ester composition 2, diisostearyl malate (Product name: COSMOL 222, manufactured by the Nisshin OilliO Group, Ltd.) and diglyceryl triisostearate (Product name: COSMOL 43V, manufactured by the Nisshin OilliO Group, Ltd.) that are each generally used as an oil in the applications of cosmetic products, in combination with various waxes.

40 g of the sample to be evaluated and 10 g of various waxes were weighed into a 100-ml glass beaker, and uniformly heated, dissolved, and mixed at 95° C., to prepare a uniform mixture.

The mixture at 95° C., prepared by the above-described method, was flowed into a 26 Φ sample bottle with a lid, and cooled to room temperature. The resultant was stored at room temperature for 12 hours to obtain a sample for evaluation of hardness maintaining or increasing ability.

(Evaluation Method)

The hardness of the sample for evaluation of hardness maintaining or increasing ability, prepared by the above-described method, was measured by using a rheometer FUDOH, 2 Φ, 2 K). The measurement results for hardness evaluation are shown in FIG. 1.

(Evaluation Results)

As shown in FIG. 1, the hardness of the sample for evaluation of hardness maintaining or increasing ability obtained by combination of the trehalose fatty acid ester compositions 2, 3, 5, and 8 of the present invention, and various waxes, exhibited equivalent or more hardness, as compared with that of the sample for evaluation of hardness maintaining or increasing ability obtained by combination of diisostearyl malate that is generally used as an oil in the applications of cosmetic product (Product name: COSMOL 222, manufactured by the Nisshin OilliO Group, Ltd.), diglyceryl triisostearate (Product name: COSMOL 43V, manufactured by the Nisshin OilliO Group, Ltd.), and various waxes. Particularly, in the case of combination with a candelilla wax, the trehalose fatty acid ester composition of the present invention exhibited about three times the hardness of that in the case of combination with an oil generally used in the applications of cosmetic products, and exhibited slightly higher hardness, as compared with the comparative sugar fatty acid ester composition 2 having sucrose as a sugar backbone.

Examples 10 to 15, and Comparative Examples 6 to 9

Evaluation of Stick Rouge (Sample to be Evaluated)

The rouges having the formulations as shown in Tables 11, 12, and 13 were prepared by the following sequential processes.

Process A: The components 1 to 20 were heated and dissolved at 95° C., and then thoroughly mixed.

Process B: The mixture obtained in the Process A was kept at 80° C., defoamed, poured into a mold, filled, cooled to room temperature, and molded.

Process C: The solid molded in the Process B was taken out of the mold, and put into a container, to obtain a stick rouge.

Furthermore, the component 11 in Tables is a sucrose stearic acid ester (trade name: Ryoto Sugar Ester S-170, manufactured by Mitsubishi-Kagaku Foods Corporation, hydroxyl value: 107), the component 12 is a sucrose oleic acid ester (trade name: Ryoto Sugar Ester O-170, manufactured by Mitsubishi-Kagaku Foods Corporation, hydroxyl value: 99), the component 13 is diisostearyl malate (trade name: COSMOL 222, manufactured by the Nisshin OilliO Group, Ltd.), and the component 14 is cetyl 2-ethylhexanoate (trade name: SALACOS 816T, manufactured by the Nisshin OilliO Group, Ltd.).

TABLE 11

Formulation of stick rouge (% by mass)

| | | EXAMPLE | | | |
|---|---|---|---|---|---|
| Component | Raw materials | 10 | 11 | 12 | 13 |
| 1 | Polyethylene wax | 10 | 10 | 10 | 10 |
| 2 | Ceresine | 5 | 5 | 5 | 5 |
| 3 | Microcrystalline wax | 3 | 3 | 3 | 3 |
| 4 | Trehalose fatty acid ester composition 2 | 5 | 4 | 0 | 0 |
| 5 | Trehalose fatty acid ester composition 3 | 0 | 0 | 5 | 0 |
| 6 | Trehalose fatty acid ester composition 4 | 0 | 0 | 0 | 5 |
| 7 | Trehalose fatty acid ester composition 5 | 0 | 0 | 0 | 0 |
| 8 | Trehalose fatty acid ester composition 6 | 0 | 1 | 0 | 0 |
| 9 | Comparative sugar fatty acid ester 2 | 0 | 0 | 0 | 0 |
| 10 | Comparative sugar fatty acid ester 5 | 0 | 0 | 0 | 0 |
| 11 | Sucrose stearic acid ester | 0 | 0 | 0 | 0 |
| 12 | Sucrose oleic acid ester | 0 | 0 | 0 | 0 |
| 13 | Diisostearyl malate | 20 | 20 | 20 | 20 |
| 14 | Cetyl 2-ethylhexanoate | 29.4 | 29.4 | 29.4 | 29.4 |
| 15 | Squalane | 18 | 18 | 18 | 18 |
| 16 | Titanium oxide | 1.5 | 1.5 | 1.5 | 1.5 |
| 17 | Red No. 202 | 3 | 3 | 3 | 3 |
| 18 | Yellow No. 4 | 2 | 2 | 2 | 2 |
| 19 | Blue No. 1 | 0.1 | 0.1 | 0.1 | 0.1 |
| 20 | Mica titanium | 3 | 3 | 3 | 3 |
| | Total | 100 | 100 | 100 | 100 |

TABLE 12

Formulation of stick rouge (% by mass)

| | | EXAMPLE | |
|---|---|---|---|
| Component | Raw materials | 14 | 15 |
| 1 | Polyethylene wax | 10 | 10 |
| 2 | Ceresine | 5 | 5 |
| 3 | Microcrystalline wax | 3 | 3 |
| 4 | Trehalose fatty acid ester composition 2 | 0 | 0 |
| 5 | Trehalose fatty acid ester composition 3 | 0 | 0 |
| 6 | Trehalose fatty acid ester composition 4 | 0 | 0 |
| 7 | Trehalose fatty acid ester composition 5 | 5 | 0 |
| 8 | Trehalose fatty acid ester composition 6 | 0 | 5 |
| 9 | Comparative sugar fatty acid ester 2 | 0 | 0 |
| 10 | Comparative sugar fatty acid ester 5 | 0 | 0 |
| 11 | Sucrose stearic acid ester | 0 | 0 |
| 12 | Sucrose oleic acid ester | 0 | 0 |
| 13 | Diisostearyl malate | 20 | 20 |
| 14 | Cetyl 2-ethylhexanoate | 29.4 | 29.4 |
| 15 | Squalane | 18 | 18 |
| 16 | Titanium oxide | 1.5 | 1.5 |
| 17 | Red No. 202 | 3 | 3 |
| 18 | Yellow No. 4 | 2 | 2 |
| 19 | Blue No. 1 | 0.1 | 0.1 |
| 20 | Mica titanium | 3 | 3 |
| | Total | 100 | 100 |

TABLE 13

Formulation of stick rouge (% by mass)

| Component | Raw materials | COMPARATIVE EXAMPLE | | | |
|---|---|---|---|---|---|
| | | 6 | 7 | 8 | 9 |
| 1 | Polyethylene wax | 10 | 10 | 10 | 10 |
| 2 | Ceresine | 5 | 5 | 5 | 5 |
| 3 | Microcrystalline wax | 3 | 3 | 3 | 3 |
| 4 | Trehalose fatty acid ester composition 2 | 0 | 0 | 0 | 0 |
| 5 | Trehalose fatty acid ester composition 3 | 0 | 0 | 0 | 0 |
| 6 | Trehalose fatty acid ester composition 4 | 0 | 0 | 0 | 0 |
| 7 | Trehalose fatty acid ester composition 5 | 0 | 0 | 0 | 0 |
| 8 | Trehalose fatty acid ester composition 6 | 0 | 0 | 0 | 0 |
| 9 | Comparative sugar fatty acid ester 2 | 0 | 0 | 0 | 4 |
| 10 | Comparative sugar fatty acid ester 5 | 0 | 0 | 0 | 1 |
| 11 | Sucrose stearic acid ester | 0 | 5 | 0 | 0 |
| 12 | Sucrose oleic acid ester | 0 | 0 | 5 | 0 |
| 13 | Diisostearyl malate | 25 | 20 | 20 | 20 |
| 14 | Cetyl 2-ethylhexanoate | 29.4 | 29.4 | 29.4 | 29.4 |
| 15 | Squalane | 18 | 18 | 18 | 18 |
| 16 | Titanium oxide | 1.5 | 1.5 | 1.5 | 1.5 |
| 17 | Red No. 202 | 3 | 3 | 3 | 3 |
| 18 | Yellow No. 4 | 2 | 2 | 2 | 2 |
| 19 | Blue No. 1 | 0.1 | 0.1 | 0.1 | 0.1 |
| 20 | Mica titanium | 3 | 3 | 3 | 3 |
| | Total | 100 | 100 | 100 | 100 |

(Evaluation Method)

Sensory evaluation of "smooth spreading ability", "moisture feeling", "make-up lasting", and "odor" was conducted on the obtained stick rouge. Furthermore, evaluation of "pigment dispersion state upon dissolution" was conducted on the mixture obtained in the Process A. Further, evaluation of "stability over time" was also conducted on the obtained stick rouge at each temperature of 5° C., 40° C., and 50° C. Hereinbelow, the evaluation methods are described.

(Sensory Evaluation Method)

The panelists for evaluation consisted of 40 women that have done make-up for 10 years or longer. They were allowed to use the rouges from EXAMPLES 10 to 15, and COMPARATIVE EXAMPLES 6 to 9 for one month, to determine the number of the panelists who answered "Good" for each item of "smooth spreading ability", "moisture feeling", "make-up lasting", and "odor". Evaluation was conducted based on the evaluation criteria in Table 14.

TABLE 14

Evaluation criteria for sensory evaluation

| Number of the panelists who answered "Good" | Evaluation | Scores |
|---|---|---|
| 31 to 40 | A | 10 |
| 21 to 30 | B | 7 |
| 11 to 20 | C | 3 |
| 0 to 10 | D | 0 |

(Evaluation Method for "Pigment Dispersion State Upon Dissolution")

A part of the mixture obtained in the Process A was left to stand in hot water (90° C.) for 30 minutes, and the settlement state of the pigment was observed. Evaluation was conducted based on the evaluation criteria in Table 15.

TABLE 15

Evaluation criteria for pigment dispersion state upon dissolution

| Settlement state after being left to stand at 90° C. for 30 minutes | Evaluation | Scores |
|---|---|---|
| No change, and no settlement | A | 10 |
| Slight change, and no problem in use | B | 7 |
| Supernatant observed | C | 3 |
| Pigment settled, and separated | D | 0 |

(Evaluation Method for "Stability Over Time")

The obtained stick rouge was taken out of the container, and stored in a thermostat bath at each temperature of 5° C., 40° C., and 50° C. The changes in appearance for up to 1 month were observed, and evaluation was conducted based on the evaluation criteria in Table 16.

TABLE 16

Evaluation criteria for stability over time

| Observation of changes in appearance for up to 1 month after storage at each temperature of 5° C., 40° C., and 50° C. | Evaluation | Scores |
|---|---|---|
| No change in any of those stored at 5° C., 40° C., and 50° C. | A | 10 |
| Slight change in any of those stored at 5° C., 40° C., and 50° C., but no problem | B | 7 |
| Change beyond the acceptable range observed | C | 3 |
| Significant change such as breakage in addition to the change in appearance observed | D | 0 |

(Evaluation Method for "Productivity")

Evaluation of handlability in the blending of trehalose fatty acid ester compositions, and the comparative sugar fatty acid ester compositions having the formulation in the Process A was conducted based on the evaluation criteria in Table 17, provided that the components 4 and 8 in EXAMPLE 11, and the components 9 and 10 in COMPARATIVE EXAMPLE 9 were used as a preliminarily prepared mixture.

TABLE 17

Evaluation criteria for productivity in formulation

| Handlability in formulation | Evaluation | Scores |
|---|---|---|
| No problem | A | 10 |
| Study on productivity required, but no problem | B | 7 |
| Problem found in productivity | C | 3 |
| Difficulty in application to production | D | 0 |

(Evaluation Results)

The evaluation results of the stick rouge are shown in Table 18. As is apparent from the results, the stick rouges in EXAMPLES 10 to 15 using the trehalose fatty acid ester compositions of the present invention were excellent in all of the items, "smooth spreading ability", "moisture feeling", "make-up lasting", "odor", "pigment dispersion state upon dissolution", "stability over time", and "productivity". Furthermore, the total evaluation score was 60 or more, indicating that they were excellent as stick rouges.

On the other hand, the stick rouges in COMPARATIVE EXAMPLES 6 and 9 were not satisfactory in the pigment dispersion state upon dissolution and the stability over time, the stick rouge in COMPARATIVE EXAMPLE 7 was not satisfactory in spreadability and stability over time, and the stick rouge in COMPARATIVE EXAMPLE 8 was not satisfactory in the odor and the stability over time.

Furthermore, the stick rouge in EXAMPLE 11, in which a part of the trehalose fatty acid ester composition 6 (component 8) in EXAMPLE 15 was replaced by a part of the trehalose fatty acid ester composition 2 (component 2), had further improved "smooth spreading ability", "stability over time", and "productivity", as compared that in EXAMPLE 15. That is, by mixing a composition having a high esterification degree (a low hydroxyl value) and a composition having a low esterification degree (a high hydroxyl value), both of dispersibility and flowability can be attained. Accordingly, it is possible to provide a cosmetic having more satisfactory quality, and it was confirmed that there is a tendency of improvement in mass production, such as increased yield, without requiring particular operations or facilities, in terms of productivity in formulation. Furthermore, using the hydroxyl value of the trehalose fatty acid ester compositions 2 and 6, from the mixing ratio thereof, the hydroxyl value of the trehalose fatty acid ester composition in EXAMPLE 11 was determined to be 81. However, as compared with EXAMPLE 13, in which only the trehalose fatty acid ester composition 4 had an equivalent hydroxyl value (94), it could be seen that moisture feeling was improved in EXAMPLE 11, thereby providing a cosmetic having a more satisfactory quality. For further reference, the analysis results of the composition of the mixture of the trehalose fatty acid ester compositions 2 and 6 used in EXAMPLE 11 are shown in Table 1.

perature of 5° C., 40° C., and 50° C. Furthermore, sensory evaluation of "smooth spreading ability", "sense of use", "gloss and uniformity of the make-up film", and "make-up lasting" were also conducted.

(Evaluation Method for "Shape-Retaining Ability and Stability Over Time")

The obtained gel rouge was stored in a thermostat bath at each temperature of 5° C., 40° C., and 50° C. The changes in appearance for up to 1 month were observed, and evaluation was conducted based on the evaluation criteria in Table 16.

(Sensory Evaluation Method)

The panelists for evaluation consisted of 40 women that have done make-up for 10 years or longer. They were allowed to use the gel rouges from EXAMPLE 16 and COMPARATIVE EXAMPLE 10 for one month, to determine the number of the panelists who answered "Good" for each item of "smooth spreading ability", "sense of use", "gloss and uniformity of the make-up film", and "make-up lasting". Evaluation was conducted based on the evaluation criteria in Table 14.

The obtained gel rouge had excellent shape-retaining ability and stability over time, had no stickiness upon application with smooth spreading ability, excellent gloss and uniformity of the make-up film, and good make-up lasting (EXAMPLE 16).

TABLE 18

Evaluation results of stick rouge

| | EXAMPLE | | | | | | COMPARATIVE EXAMPLE | | | |
|---|---|---|---|---|---|---|---|---|---|---|
| | 10 | 11 | 12 | 13 | 14 | 15 | 6 | 7 | 8 | 9 |
| Hydroxyl value of trehalose fatty acid ester composition | 42 | 81 | 57 | 94 | 142 | 238 | | | | |
| Ingredient I | 4.5 | 21.7 | 12.4 | 27.3 | 50.5 | 73.2 | | | | |
| Ingredient II | 83.4 | 63 | 66.8 | 47.4 | 22.9 | 5 | | | | |
| Evaluation items | Evaluation results | | | | | | | | | |
| Smooth spreading ability | A | A | A | A | B | B | A | D | B | A |
| Moisture feeling | B | A | B | B | A | A | B | B | B | B |
| Make-up lasting | A | A | A | A | A | A | A | A | A | A |
| Odor | B | B | B | B | B | B | B | B | D | B |
| Pigment dispersion state upon dissolution | A | A | A | A | A | A | D | A | A | C |
| Stability over time | A | A | A | A | A | B | C | D | D | C |
| Productivity | A | A | A | A | B | B | A | A | B | A |
| Total evaluation: Note 3) | 64 | 67 | 64 | 64 | 61 | 61 | 47 | 44 | 41 | 50 |

Note 3) Total evaluation means the total score of the evaluation results, as calculated based on the scoring criteria in <Table 15>, <Table 16>, and <Table 17>. A score of 60 or more is indicative of "Excellent" property.

Example 16 and Comparative Example 10

Preparation and Evaluation of Gel Rouge

A gel rouge of the formulation as shown in Table 19 was prepared in accordance with the following sequential processes.

Process A: The components 1 to 7 were heated and dissolved at 90° C., and mixed.

Process B: The components 8 to 11 were added to the mixture obtained in the Process A, and mixed and stirred at 90° C.

Process C: The mixture obtained in the Process B was kept at 80° C., defoamed, put into a container, and cooled to room temperature, to obtain a gel rouge.

(Evaluation Method)

Evaluation of "shape-retaining ability and stability over time" was conducted on the obtained gel rouge at each tem- However, the gel rouge prepared by using diisostearyl malate instead of the trehalose fatty acid ester composition 3 of the present invention as the component 3 could not satisfy all the properties (COMPARATIVE EXAMPLE 10).

TABLE 19

Formulation of gel rouge (% by mass)

| Component | Raw materials | EXAMPLE 16 | COMPARATIVE EXAMPLE 10 |
|---|---|---|---|
| 1 | Candelilla wax | 6 | 6 |
| 2 | Microcrystalline wax | 2 | 2 |
| 3 | Trehalose fatty acid ester composition 3 | 40 | 0 |
| 4 | Diisostearyl malate | 0 | 40 |
| 5 | Isotridecyl isononanoate | 20 | 20 |
| 6 | Octyl palmitate | 10 | 10 |

TABLE 19-continued

Formulation of gel rouge (% by mass)

| Component | Raw materials | EXAMPLE 16 | COMPARATIVE EXAMPLE 10 |
|---|---|---|---|
| 7 | Natural vitamin E | 0.1 | 0.1 |
| 8 | Talc | 4.9 | 4.9 |
| 9 | Anhydrous silicic acid | 2 | 2 |
| 10 | Mica titanium | 12 | 12 |
| 11 | Red No. 202 | 3 | 3 |
| | Total | 100 | 100 |

Evaluation results for gel rouge

| | | | |
|---|---|---|---|
| Shape-retaining ability and stability over time | | A | C |
| Smooth spreading ability | | A | C |
| Sense of use | | B | C |
| Gloss and uniformity of the make-up film | | A | B |
| Make-up lasting | | B | C |

Example 17 and Comparative Example 11

Preparation and Evaluation of Stick Rouge

A stick rouge of the formulation as shown in Table 20 was prepared in accordance with the following sequential processes.

Process A: The components 1 to 9 were heated and dissolved at 100° C., and mixed.

Process B: The components 10 to 12 were added to the mixture obtained in the Process A, and stirred under heating at 100° C.

Process C: The mixture obtained in the Process B was kept at 80° C., defoamed, put into a container, and cooled to room temperature, to obtain a stick rouge.

(Evaluation Method)

Evaluation of "shape-retaining ability and stability over time" was conducted on the obtained stick rouge at each temperature of 5° C., 40° C., and 50° C. Furthermore, sensory evaluation of "smooth spreading ability", "sense of use", "gloss and uniformity of the make-up film", and "make-up lasting" were also conducted.

(Evaluation Method for "Shape-Retaining Ability and Stability Over Time")

The obtained stick rouge was stored in a thermostat bath at each temperature of 5° C., 40° C., and 50° C. The changes in appearance up to 1 month were observed, and evaluation was conducted based on the evaluation criteria in Table 16.

(Sensory Evaluation Method)

The panelists for evaluation consisted of 40 women that have done make-up for 10 years or longer. They were allowed to use the stick rouges from EXAMPLE 17 and COMPARATIVE EXAMPLE 11 for one month, to determine the number of the panelists who answered "Good" for each item of "smooth spreading ability", "sense of use", "gloss and uniformity of the make-up film", and "make-up lasting". Evaluation was conducted based on the evaluation criteria in Table 14.

The obtained stick rouge had excellent shape-retaining ability and stability over time, had no stickiness upon application with smooth spreading ability, excellent gloss and uniformity of the make-up film, and good make-up lasting (EXAMPLE 17).

However, the stick rouge prepared by using diglyceryl triisostearate instead of the trehalose fatty acid ester composition 4 of the present invention as the component 4 could not satisfy all the properties (COMPARATIVE EXAMPLE 11).

TABLE 20

Formulation of stick rouge (% by mass)

| Component | Raw materials | EXAMPLE 17 | COMPARATIVE EXAMPLE 11 |
|---|---|---|---|
| 1 | Candelilla wax | 5 | 5 |
| 2 | Polyethylene wax | 4 | 4 |
| 3 | Ethylene/propylene copolymer | 4 | 4 |
| 4 | Trehalose fatty acid ester composition 4 | 35 | 0 |
| 5 | Diglyceryl triisostearate | 0 | 35 |
| 6 | Cetyl 2-ethylhexanoate | 10 | 10 |
| 7 | Glyceryl tri 2-ethylhexanoate | 20 | 20 |
| 8 | Hydrogenated polybutene | 4.9 | 4.9 |
| 9 | Natural viamin E | 0.1 | 0.1 |
| 10 | Anhydrous silicic acid | 2 | 2 |
| 11 | Mica titanium | 12 | 12 |
| 12 | Red No. 202 | 3 | 3 |
| | Total | 100 | 100 |

Evaluation results for stick rouge

| | | | |
|---|---|---|---|
| Shape-retaining ability and stability over time | | A | C |
| Smooth spreading ability | | A | B |
| Sense of use | | A | B |
| Gloss and uniformity of the make-up film | | A | C |
| Make-up lasting | | A | B |

Example 18

Preparation and Evaluation of Powder Foundation

A powder foundation of the formulation as shown in Table 21 was prepared in accordance with the following sequential processes Process A: The components 1 to 8 were uniformly mixed and dispersed at room temperature.

Process B: The components 9 to 14 were added to the mixture dispersion obtained in the Process A, and uniformly mixed at room temperature.

Process C: The mixture obtained in the Process B was ground, and filled in a container, to obtain a powder foundation.

The obtained powder foundation had excellent shape retaining ability and stability over time, good moisture feeling with smooth spreading ability, and good make-up lasting.

TABLE 21

| Component | Raw materials | % by mass |
|---|---|---|
| 1 | Talc | 53 |
| 2 | Sericite | 20 |
| 3 | Nylon powder | 5 |
| 4 | Aluminum stearate | 5 |
| 5 | Titanium oxide | 5 |
| 6 | Red iron oxide | 0.3 |
| 7 | Yellow iron oxide | 1.5 |
| 8 | Black iron oxide | 0.2 |
| 9 | Dimethyl polysiloxane (molecular weight: 2000) | 5 |
| 10 | Trehalose fatty acid ester composition 3 | 2 |
| 11 | Isononyl isononanoate | 2 |

TABLE 21-continued

| Component | Raw materials | % by mass |
|---|---|---|
| 12 | Methyl paraoxybenzoate | 0.5 |
| 13 | Phenozyethanol | 0.3 |
| 14 | Fragrance | 0.2 |
| | Total | 100 |

Example 19

Preparation and Evaluation of Liquid Foundation

A liquid foundation of the formulation as shown in Table 22 was prepared in accordance with the following sequential processes.

Process A: The components 1 to 11 were mixed at room temperature.

Process B: The components 12 to 15 were added to the mixture obtained in the Process A, and uniformly dispersed with a homomixer at room temperature, to obtain a liquid foundation.

The obtained liquid foundation had excellent dispersibility and stability over time, no stickiness, good moisture feeling, and good make-up lasting with smooth spreading ability.

TABLE 22

| Component | Raw materials | % by mass |
|---|---|---|
| 1 | Decamethyl cyclopentasiloxane | 17 |
| 2 | Polyoxyalkylene modified silicone | 5 |
| 3 | Octyl palmitate | 2 |
| 4 | Trehalose fatty acid ester composition 4 | 5 |
| 5 | Squalane | 5 |
| 6 | Titanium oxide | 6 |
| 7 | Red iron oxide | 0.3 |
| 8 | Yellow iron oxide | 2 |
| 9 | Black iron oxide | 0.2 |
| 10 | Talc | 5 |
| 11 | Spherical silica | 5 |
| 12 | Purified water | 40 |
| 13 | 1,3-Butylene glycol | 5 |
| 14 | Glycerin | 2 |
| 15 | Methyl paraoxybenzoate | 0.5 |
| | Total | 100 |

Example 20

Preparation and Evaluation of Stick Concealer

A stick concealer of the formulation as shown in Table 23 was prepared in accordance with the following sequential processes.

Process A: The components 1 to 12 were heated and dissolved at 100° C., and mixed.

Process B: The mixture obtained in the Process A was kept at 80° C., defoamed, put into a container, and cooled to room temperature, to obtain a stick concealer.

The obtained stick concealer had excellent shape-retaining ability and stability over time, no stickiness, excellent shielding effect, and good make-up lasting.

TABLE 23

| Component | Raw materials | % by mass |
|---|---|---|
| 1 | Polyethylene wax | 5 |
| 2 | Ceresine | 5 |
| 3 | Paraffin | 8 |
| 4 | Isononyl isononanoate | 32.7 |
| 5 | Polybutene | 5 |
| 6 | Dimethyl polysiloxane | 3 |
| 7 | Trehalose fatty acid ester composition 3 | 5 |
| 8 | Titanium oxide | 20 |
| 9 | Red iron oxide | 0.8 |
| 10 | Yellow iron oxide | 5 |
| 11 | Black iron oxide | 0.5 |
| 12 | Talc | 10 |
| | Total | 100 |

Example 21

Preparation and Evaluation of Lip Gloss

A lip gloss of the formulation as shown in Table 24 was prepared in accordance with the following sequential processes.

Process A: The components 1 to 8 were heated and dissolved at 85° C., and mixed.

Process B: The mixture obtained in the Process A was kept at 80° C., defoamed, put into a container, and cooled to room temperature, to obtain a lip gloss.

The obtained lip gloss had good stability over time, excellent gloss, and good make-up lasting.

TABLE 24

| Component | Raw materials | % by mass |
|---|---|---|
| 1 | Trehalose fatty acid ester composition 5 | 50.5 |
| 2 | Polybutene | 10 |
| 3 | Diisostearyl malate | 15 |
| 4 | Methylphenyl polysiloxane | 20 |
| 5 | Dextrin palmitate | 2 |
| 6 | Red No. 202 | 0.2 |
| 7 | Yellow iron oxide | 0.3 |
| 8 | Mica titanium | 2 |
| | Total | 100 |

Example 22

Preparation and Evaluation of Eye-Color Pencil

An eye-color pencil of the formulation as shown in Table 25 was prepared in accordance with the following sequential processes Process A: The components 1 to 10 were heated and dissolved at 85° C., and mixed.

Process B: The mixture obtained in the Process A was kept at 80° C., defoamed, put into a shift hole of the back end of a cylindrical shift made from a resin (back filling), cooled, and solidified, to obtain an eye-color pencil.

The obtained eye-color pencil had excellent shape-retaining ability and stability over time, good gloss, and good make-up lasting.

TABLE 25

| Component | Raw materials | % by mass |
| --- | --- | --- |
| 1 | Ceresine | 6 |
| 2 | Microcrystalline wax | 5 |
| 3 | Candelilla wax | 4 |
| 4 | Bee wax | 5 |
| 5 | *Macadamia* nut oil | 10.4 |
| 6 | Trehalose fatty acid ester composition 5 | 30 |
| 7 | Diisostearyl malate | 7 |
| 7 | Natural vitamin E | 0.1 |
| 8 | Mica | 3 |
| 9 | Cobalt blue | 1.5 |
| 10 | Mica titanium | 28 |
| | Total | 100 |

Example 23

Preparation and Evaluation of Eye Cream

An eye cream of the formulation as shown in Table 26 was prepared in accordance with the following sequential processes.

Process A: The components 1 to 8 were heated and dissolved at 80° C., and mixed.

Process B: The components 9 to 14 were heated to 80° C., added to the mixture obtained in the Process A, and emulsified.

Process C: The mixture obtained in the Process B was cooled, to obtain an eye cream.

The eye cream had excellent stability over time, and excellent refreshness and lastingness of moisture feeling.

TABLE 26

| Component | Raw materials | % by mass |
| --- | --- | --- |
| 1 | Trehalose fatty acid ester composition 5 | 0.05 |
| 2 | Polyoxyethylene (20) sorbitan trioleate | 0.1 |
| 3 | Di(phytosteryl/behenyl alcohol/octyldodecyl) N-Lauroyl-L-glutamate | 0.5 |
| 4 | Microcrystalline wax | 0.5 |
| 5 | Polybutene | 1.5 |
| 6 | Stearyl alcohol | 2.5 |
| 7 | Trehalose fatty acid ester composition 2 | 1 |
| 8 | Dimethyl polysiloxane | 0.5 |
| 9 | Diprophylene glycol | 5 |
| 10 | Glycerin | 5 |
| 11 | Sodium alginate Black iron oxide | 0.1 |
| 12 | Ethyl paraoxybenzoate | 0.1 |
| 13 | Purified water | 83.13 |
| 14 | Fragrance | 0.02 |
| | Total | 100 |

Example 24

Preparation and Evaluation of Cleansing Oil

A cleansing oil of the formulation as shown in Table 27 was prepared in accordance with the following sequential processes.

Process A: The components 1 to 8 were heated and dissolved at 80° C., and mixed.

Process B: The mixture obtained in the Process A was cooled, to obtain a cleansing oil.

The obtained cleansing oil had excellent stability over time, good cleansing effect, and good rinsability.

TABLE 27

| Component | Raw materials | % by mass |
| --- | --- | --- |
| 1 | Liquid paraffin | 84 |
| 2 | Isononyl isononanoate | 4.8 |
| 3 | Trehalose fatty acid ester composition 5 | 5 |
| 4 | Polysorbate 85 | 5 |
| 5 | Glycerin | 0.5 |
| 6 | Purified water | 0.5 |
| 7 | 1,3-Butylene glycol | 0.1 |
| 8 | Fragrance | 0.1 |
| | Total | 100 |

Example 25

Preparation and Evaluation of Cleansing Foam

A cleansing foam of the formulation as shown in Table 28 was prepared in accordance with the following sequential processes.

Process A: The components 1 to 7 were heated and dissolved at 80° C., and mixed.

Process B: The components 8 to 13 were mixed at room temperature.

Process C: The mixture obtained in the Process A was kept at 80° C., and the mixture obtained in the Process B was added thereto, and emulsified Process D: The mixture obtained in the Process C was cooled, and the component 14 was added thereto, to obtain a cleansing foam.

The obtained cleansing foam had excellent stability over time, refreshness after washing, and good washability.

TABLE 28

| Component | Raw materials | % by mass |
| --- | --- | --- |
| 1 | Stearic acid | 10 |
| 2 | Palmitic acid | 10 |
| 3 | Myristic acid | 12 |
| 4 | Lauric acid | 4 |
| 5 | Trehalose fatty acid ester composition 4 | 2 |
| 6 | Polysorbate 80 | 2 |
| 7 | Polyethylene glycol 1500 | 10 |
| 8 | 1,3-Butylene glycol | 4 |
| 9 | Purified water | 24.6 |
| 10 | Potassium hydroxide | 6 |
| 11 | Glycerin | 15 |
| 12 | Tetrasodium edetate | 0.2 |
| 13 | Methyl paraoxybenzoate | 0.19 |
| 14 | Fragrance | 0.01 |
| | Total | 100 |

Example 26

Preparation and Evaluation of W/O Type UV Cream

A W/O type UV cream of the formulation as shown in Table 29 was prepared in accordance with the following sequential processes.

Process A: The components 1 to 9 were mixed at room temperature.

Process B: The components 10 to 13 were added to the mixture obtained in the Process A, and uniformly dispersed with a homomixer at room temperature, to obtain a W/O type UV cream.

The obtained W/O type UV cream had excellent dispersibility and stability over time, no stickiness, good moisture feeling, and good UV shielding effect.

TABLE 29

| Component | Raw materials | % by mass |
| --- | --- | --- |
| 1 | Decamethyl cyclopentasiloxane | 29.7 |
| 2 | Polyoxyalkylene modified silicone | 5 |
| 3 | Glyceryl tri 2-ethylhexanoate | 5 |
| 4 | Trehalose fatty acid ester composition 4 | 3 |
| 5 | Diglyceryl distearate | 1 |
| 6 | Octyl paramethoxycinnamate | 5 |
| 7 | Particualte titanium oxide | 15 |
| 8 | Particulate oxide zinc | 5 |
| 9 | Nylon powder | 5 |
| 10 | Purified water | 20 |
| 11 | Diprophylene glycol | 5 |
| 12 | Methyl paraoxybenzoate | 0.3 |
| 13 | Sorbitol | 1 |
|  | Total | 100 |

Example 27

Preparation and Evaluation of O/W Type Whitening Cream

An O/W type whitening cream of the formulation as shown in Table 30 was prepared in accordance with the following sequential processes.

Process A: The components 1 to 8 were heated and dissolved at 80° C., and mixed.

Process B: The components 9 to 15 were mixed at 80° C.

Process C: The mixture obtained in the Process B was added to the mixture obtained in the Process A at 80° C., and emulsified.

Process D: The mixture obtained in the Process C was cooled to room temperature, to obtain an O/W type whitening cream.

The obtained O/W type whitening cream had excellent stability over time, no stickiness, and thick sense of use with smooth spreading ability. Furthermore, stability of the whitening components was good.

TABLE 30

| Component | Raw materials | % by mass |
| --- | --- | --- |
| 1 | Dimethyl polysiloxane | 3 |
| 2 | Squalane | 5 |
| 3 | Glyceryl tri 2-ethylhexanoate | 3 |
| 4 | Polyoxyalkylene modified silicone | 1 |
| 5 | Diglyceryl distearate | 1 |
| 6 | Trehalose fatty acid ester composition 8 | 2 |
| 7 | Polysorbate 80 | 3 |
| 8 | Stearic acid | 1 |
| 9 | Purified water | 66.4 |
| 10 | 1,3-Butylene glycol | 5 |
| 11 | Glycerin | 5 |
| 12 | Gum xanthane | 0.1 |
| 13 | Magnesium phosphate ascorbate | 3 |
| 14 | Triethanol amine | 1 |
| 15 | Methyl paraoxybenzoate | 0.5 |
|  | Total | 100 |

Example 28

Preparation and Evaluation of Clay Wax

A clay wax of the formulation as shown in Table 31 was prepared in accordance with the following sequential processes.

Process A: The components 1 to 9 were heated and dissolved at 80° C., and mixed.

Process B: The mixture obtained in the Process A was flowed into a container at 80° C., and cooled, to obtain a clay wax.

The obtained clay wax had excellent stability over time, no stickiness, and good setting property.

TABLE 31

| Component | Raw materials | % by mass |
| --- | --- | --- |
| 1 | Liquid paraffin | 54.3 |
| 2 | Vaseline | 10 |
| 3 | Talc | 30 |
| 4 | Quaternium-18 hectorite | 0.5 |
| 5 | Trehalose fatty acid ester composition 3 | 3 |
| 6 | Candelilla wax | 2 |
| 7 | Propyl paraoxybenzoate | 0.09 |
| 8 | Natural viamin E | 0.1 |
| 9 | Fragrance | 0.01 |
|  | Total | 100 |

Example 29

Preparation and Evaluation of Nail Polish

A nail polish of the formulation as shown in Table 32 was prepared in accordance with the following sequential processes.

Process A: The components 1 to 12 were thoroughly mixed at room temperature.

Process B: The mixture obtained in the Process A was filled into a container, to obtain a nail polish.

The obtained nail polish had excellent stability over time, could be easily and uniformly applied without stain, and was rapidly dried. Furthermore, the durability of the applied film after drying was good.

TABLE 32

| Component | Raw materials | % by mass |
| --- | --- | --- |
| 1 | Nitrocellulose | 10 |
| 2 | Alkyd resin | 10 |
| 3 | Acetyl tributyl citrate | 5 |
| 4 | Ethyl acetate | 25 |
| 5 | Butyl acetate | 41.9 |
| 6 | Ethyl alcohol | 5 |
| 7 | Red No. 202 | 0.2 |
| 8 | Yellow iron oxide | 0.3 |
| 9 | Mica titanium | 2 |
| 10 | Trehalose fatty acid ester composition 3 | 0.5 |
| 11 | Natural viamin E | 0.09 |
| 12 | Fragrance | 0.01 |
|  | Total | 100 |

As described above, it was confirmed that the trehalose fatty acid ester composition of the present invention has excellent pigment dispersibility, and cosmetics obtained by blending the composition therein are all excellent in sense of use, make-up lasting, odor, and stability over time. Furthermore, it was also confirmed that since the cosmetics do not require particular operations or facilities for their preparation, and can be prepared by a conventionally known method, it could provide a cosmetic that is excellent in terms of cost.

INDUSTRIAL APPLICABILITY

The trehalose fatty acid ester composition of the present invention can be used as a pigment dispersant to widely provide a variety of cosmetics having higher quality with low cost, and therefore, the present invention would be useful in various industries relating to a variety of cosmetic products.

The invention claimed is:

1. A trehalose fatty acid ester composition prepared by esterifying trehalose with a fatty acid having 8 to 22 carbon atoms, the composition has a hydroxyl value of 20 to 500, and the total amount of a diester, a triester, a tetraester and a pentaester of 10 to 95% by area as measured by high-performance liquid chromatography, and a hexaester, a heptaester, or an octaester of trehalose.

2. A trehalose fatty acid ester composition obtained from trehalose and a fatty acid having 8 to 22 carbon atoms, the composition has a total amount of a diester, a triester, and a tetraester of 2 to 40% by area as measured by high-performance liquid chromatography, and has a total amount of a hexaester, a heptaester, and an octaester of 30 to 98% by area as measured by high-performance liquid chromatography.

3. The trehalose fatty acid ester composition according to claim 1 or 2, wherein the fatty acid having 8 to 22 carbon atoms is isostearic acid.

4. The trehalose fatty acid ester composition according to claims 1 or 2, which is used as a dispersant.

5. A cosmetic comprising the trehalose fatty acid ester composition of any one of claims 1 or 2.

* * * * *